(12) United States Patent
Karmon

(10) Patent No.: US 7,749,267 B2
(45) Date of Patent: Jul. 6, 2010

(54) EXPANDABLE DEVICES AND METHODS FOR TISSUE EXPANSION, REGENERATION AND FIXATION

(76) Inventor: Ben-Zion Karmon, 24 Hanissiem St., Petach Tikva 49550 (IL)

( * ) Notice: Subject to any disclaimer, the term of this patent is extended or adjusted under 35 U.S.C. 154(b) by 522 days.

(21) Appl. No.: 11/126,208

(22) Filed: May 11, 2005

(65) Prior Publication Data

US 2005/0209595 A1 Sep. 22, 2005

Related U.S. Application Data

(63) Continuation-in-part of application No. PCT/IL03/000951, filed on Nov. 12, 2003, now abandoned, which is a continuation-in-part of application No. 10/291,477, filed on Nov. 12, 2002, now abandoned, which is a continuation-in-part of application No. PCT/IL01/00408, filed on May 9, 2001, now abandoned, which is a continuation-in-part of application No. 09/567,471, filed on May 9, 2000.

(51) Int. Cl.
*A61F 2/02* (2006.01)
*A61F 2/28* (2006.01)

(52) U.S. Cl. ............. 623/16.11; 623/23.61; 623/23.72; 623/23.75; 623/23.76; 606/86 R

(58) Field of Classification Search ........................ None
See application file for complete search history.

(56) References Cited

U.S. PATENT DOCUMENTS

| | | | |
|---|---|---|---|
| 3,875,595 A | 4/1975 | Froning | |
| 4,521,192 A | 6/1985 | Linkow | |
| 4,787,906 A * | 11/1988 | Haris | 623/23.72 |
| 4,843,112 A | 6/1989 | Gerhart et al. | |
| 4,863,472 A * | 9/1989 | Tormala et al. | 623/23.58 |
| 4,969,888 A | 11/1990 | Scholten et al. | |
| 5,108,404 A | 4/1992 | Scholten et al. | |
| 5,146,933 A | 9/1992 | Boyd | |
| 5,254,089 A | 10/1993 | Wang | |
| 5,368,046 A | 11/1994 | Scarfone et al. | |
| 5,496,368 A | 3/1996 | Wiese | |
| 5,549,676 A | 8/1996 | Johnson | |
| 5,549,679 A | 8/1996 | Kuslich | |

(Continued)

FOREIGN PATENT DOCUMENTS

EP 411767 2/1991

(Continued)

*Primary Examiner*—David H Willse
*Assistant Examiner*—Javier G Blanco
(74) *Attorney, Agent, or Firm*—Mark M. Friedman

(57) ABSTRACT

Expandable devices and methods for treating and enlarging a tissue, an organ or a cavity. The device is composed of a hollow expanding pouch made of a resorbable material or a perforated material that can be attached to a filling element. The pouch can be filled with a biocompatible materials, one or more times in few days interval, after the insertion of the device. While filling the pouch every few days the tissue expands and the filling material if it is bioactive start to function. The devices allow immediate direct contact between the filling material and the tissue. These devices and methods can be used for example for: horizontal and vertical bone augmentation in the jaws, soft tissue augmentation, fixating bone fractures etc.

11 Claims, 8 Drawing Sheets

U.S. PATENT DOCUMENTS

| | | |
|---|---|---|
| 5,562,736 A | 10/1996 | Ray et al. |
| 5,571,189 A | 11/1996 | Kuslich |
| 5,674,295 A | 10/1997 | Ray et al. |
| 5,685,716 A | 11/1997 | Linkow |
| 5,711,315 A * | 1/1998 | Jerusalmy ................... 128/898 |
| 5,741,223 A | 4/1998 | Janzen et al. |
| 5,746,762 A | 5/1998 | Bass |
| 5,792,400 A | 8/1998 | Talja et al. |
| 5,827,289 A | 10/1998 | Reiley et al. |
| 5,882,353 A | 3/1999 | VanBeek et al. |
| 5,919,234 A * | 7/1999 | Lemperle et al. ......... 623/23.72 |
| 5,972,015 A | 10/1999 | Scribner et al. |
| 6,027,744 A | 2/2000 | Vacanti et al. |
| 6,045,497 A | 4/2000 | Schweich et al. |
| 6,077,076 A * | 6/2000 | Comfort ..................... 433/173 |
| 6,127,597 A | 10/2000 | Beyar et al. |
| 6,206,930 B1 | 3/2001 | Burg et al. |
| 6,214,012 B1 | 4/2001 | Karpman et al. |
| 6,264,695 B1 | 7/2001 | Stoy |
| 6,740,093 B2 | 5/2004 | Hochschuler et al. |
| 2001/0014831 A1 * | 8/2001 | Scarborough ............ 623/23.51 |

FOREIGN PATENT DOCUMENTS

| | | |
|---|---|---|
| WO | WO 96/24310 | 8/1996 |

* cited by examiner

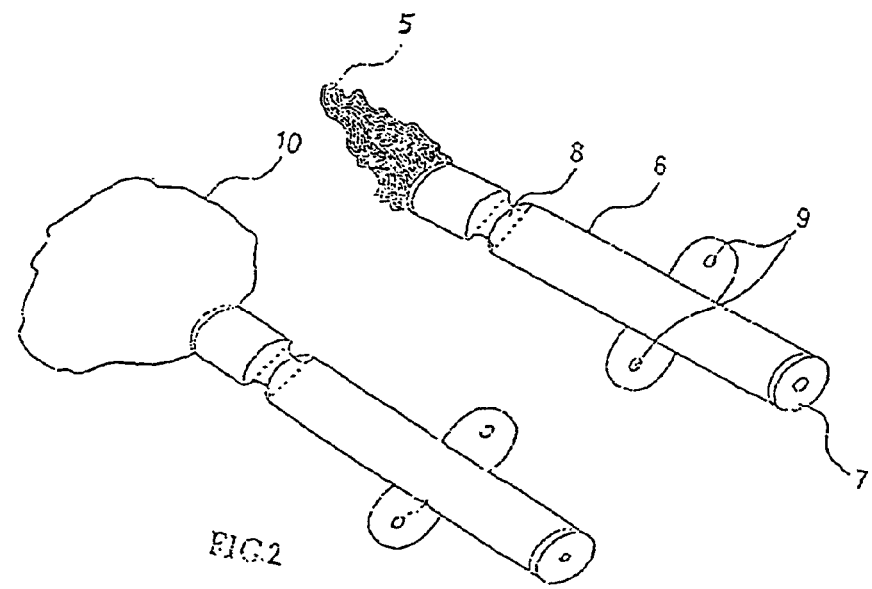
FIG. 1
FIG. 2
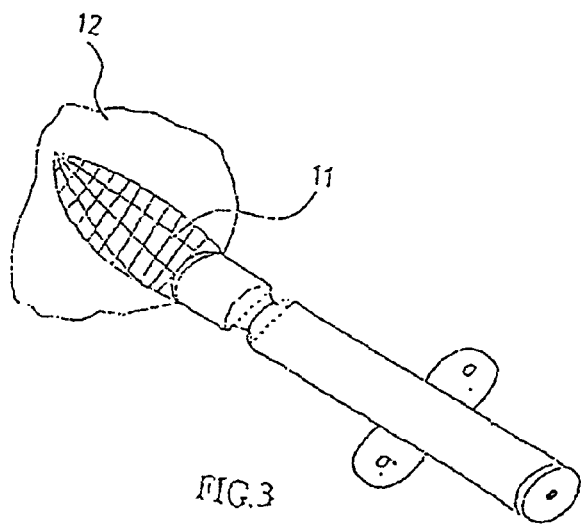
FIG. 3
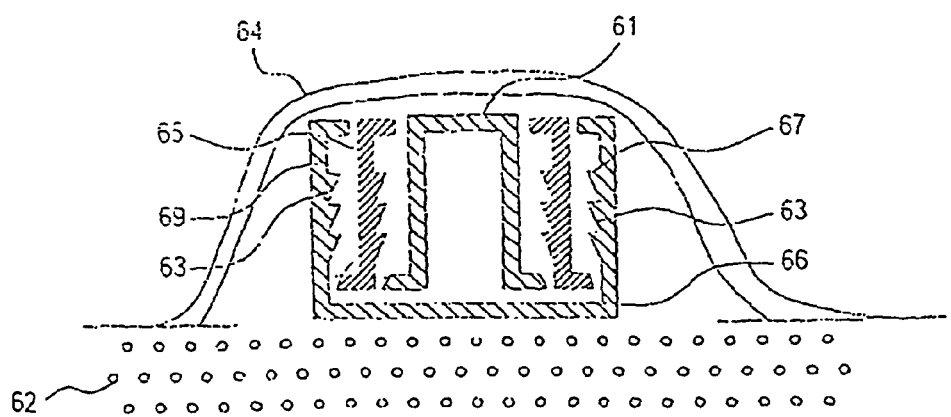
FIG. 4

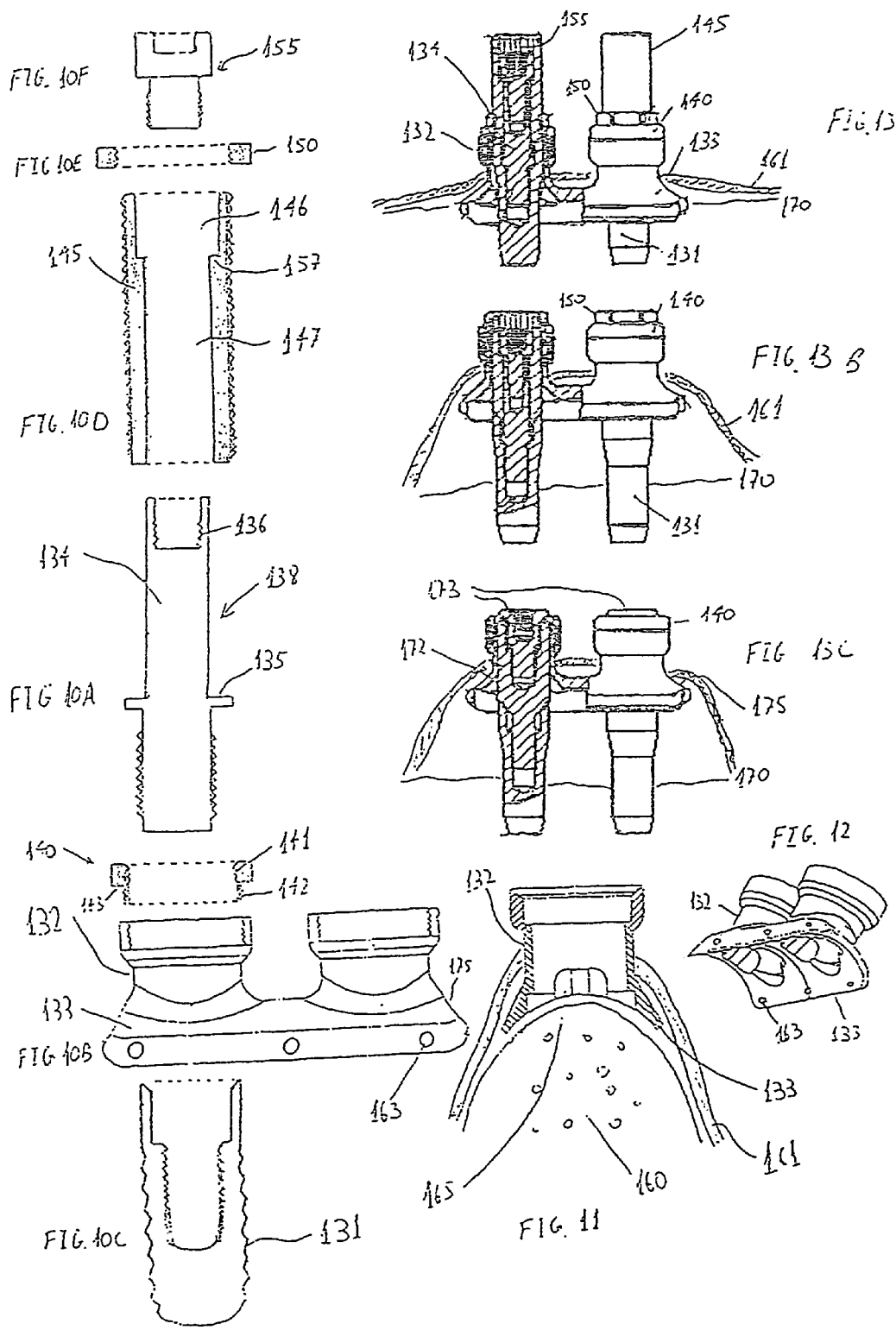

EXPANDABLE DEVICES AND METHODS FOR TISSUE EXPANSION, REGENERATION AND FIXATION

This application is a Continuation-in-Part of PCT/IL2003/000951 filed Nov. 12, 2003, abandoned, which is a Continuation-in Part of U.S. Ser. No. 10/291,477 filed Nov. 12, 2002, abandoned, which is a Continuation-in-Part of PCT/IL2001/00408 filed May 9, 2001, abandoned, which is a Continuation-in-Part of U.S. Ser. No. 09/567,471 filed May 9, 2000, pending.

FIELD AND BACKGROUND OF THE INVENTION

The present invention relates to an improved methods and devices for treating and healing a tissue deficiency or pathology in a living human or animal body. The methods and the devices combine a mechanical action and a biological action.

For example, the present invention can be used for guided bone regeneration in the jaws as part of dental treatment with dental implants. It can be used to fixate bones, to fill bone cavities and to expand bone cavities.

The present invention consists of an expansion device that can include a bioresorbable film or a perforated film and a method for tissue regeneration. In order to clarify the principles of the present invention the following description will focus on two implementations: bone regeneration in the jaws preceding dental treatment with dental implants, and fixating bone fractures. The same principles may be applied to other tissues and other organs and other areas of the body.

Treatment of edentulous patients with osseointegrated fixtures made of titanium is a well known procedure in the art. The procedure includes installing a fixture in the alveolar bone of an at least partially edentulous jaw. Usually several months are required for proper healing after fixture installation.

After healing, an abutment is installed on the upper portion of the fixture. After several weeks, an artificial tooth may be mounted on the abutment and the procedure is complete.

Installation of implants requires sufficient alveolar bone, generally about 10 mm height and 6 mm width.

When a tooth is removed, the alveolar bone is gradually resorbed because of the absence of stimulus of ossification-inducing pressure from the teeth. As the resorption process advances, the size of the bone gets reduced, i.e. the bone on which the dental roots are positioned—the alveolar ridge starts shrinking.

The absence of just one tooth can cause modifications throughout the dental arch and even prompt a possible softening (loss of insertion) which may cause the loss of other teeth. The absence of several teeth aggravates the problem. Bone loss may finally modify the patient's appearance and, depending on the loss, may make him incapable of receiving bridges, implants or even dentures.

It is then necessary to carry out several surgical operations to reconstruct the alveolar ridge of the maxilla or mandible.

Although these methods of surgical reconstruction have been successfully performed, this type of operation has had drawbacks. Certain methods have involved opening the mucoperiosteal tissue along the entire length of the atrophic alveolar ridge and then placing a bone graft material and a membrane on top of the graft and then suturing the delicate mucoperiosteal tissue back together to cover the membrane. The role of the membrane is to maintain the bone graft in its place and to prevent the mucoepithelium from growing into the graft and interfering with the process of bone regeneration. This surgical operation has had drawbacks because it is difficult to stretch and cover the augmented ridge resulting in high prevalence of membrane exposure and infection.

The present invention is unique because it simultaneously regenerates the soft and the hard tissues, therefore avoids most of the foregoing drawbacks and permits a more simplified and effective means for bone regeneration:

This invention relates also to methods and devices for correcting bone abnormalities and involves use of an inflatable device, which can be inserted into a prepared cavity in bone or to be adjacent bones. The device is inflated using bone replacement material to expand and fill the cavity. The device can be inserted subperiostealy to enlarge the bone.

U.S. Pat. Nos. 5,108,404 and 4,969,888 to Scholten et al. describe a system for fixing osteoporotic bone using an inflatable balloon, which compacts the bone to form a cavity into which bone cement is injected after the balloon is withdrawn. The invention requires the use of fluoroscopy to monitor the injection and to help guard against cement leakage through fissures in bone. Unfortunately, such leakage is known to occur in spite of these precautions. Since such leakage may cause serious injury, including paralysis, an improved device and method is needed. U.S. Pat. No. 5,972,015 to Scribner et al. describes a system of deploying a catheter tube into the interior of a vertebra and expanding a specially configured nonporous balloon there within to compact cancellous bone to form a cavity. The Scribner U.S. Pat. No. 5,972,015 approach utilizes a non-porous balloon which is inflated within the bone to cause compression. The cavity thus formed may then be filled with bone cement. Unfortunately, the bag used by Scribner may be ruptured during expansion to compact cancellous bone due to sharp projections found within the cavity to be expanded. Filling the cavity eventually formed could allow leakage of bone cement out of the bone against vessels or nerves which may cause undesirable complications.

U.S. Pat. Nos. 5,549,679 and 5,571,189 to Kuslich describe a device and method for stabilizing the spinal segment with an expandable, porous fabric implant for insertion into the interior of a reamed out disc which is packed with material to facilitate bony fusion. The device of Kuslich prevents direct contact between the filled material and the bone. In the present invention, an improved device is used to correct bone abnormalities including, but not limited to, bone tumors and cysts, tibial plateau fractures, avascular necrosis of the femoral head and compression fractures of the spine.

The present invention involves an improvement of all of the previous techniques and avoids complications that could occur with the system of U.S. Pat. No. 5,972,015. Therefore, it is an object of this invention to provide a method and apparatus that has some or all of these properties.

SUMMARY OF THE INVENTION

The present invention provides a method and device by which, as the device is enlarged, a space is created to allow tissue ingrowth. The space created can be filled with a biocompatible material. The enlargement and filling can be done simultaneously and the filling can be the cause for the expansion of the device. The biocompatible material can be a bioactive material like a drug or an inert material.

The device is made of a pouch or compartment that can be filled preferably through a filling element with the biocompatible material. The pouch is made fully or partially of a bioresorbable material or a perforated material and it acts like a balloon that expands as it is filled with the biocompatible material. The pouch preferably has at least one region that allows tissue ingrowth or immediate direct contact between the filled material and the surrounding tissue and at least one region that prevents contact between the filled material and the surrounding tissue. The region that allows the contact can be perforated with a large hole or several holes of several hundreds of microns or can be a completely open region or wall. The filling material preferably includes rigid particles or material which becomes rigid so the direct and immediate contact results in continuous mass of material extending from the internal space of the device to the tissue. In the present invention a space in the body is created by the expandable or inflatable device. This space is preferably filled with a biocompatible/bioactive material. The expansion of the expandable device can be by the filling with biocompatible material like bone cement. The device is preferably configured to allow the filling. The space filled with the filling material is not isolated from the tissue so part of the filling material is touching the tissue. This contact is by passing through the big holes or touching the tissue in a region of the device that is completely open. Part of the material is released through walls of the device so the material touching the tissue and the material inside the device are forming one continuous substance. There are prior art devices that allow diffusion of drugs through their walls. These devices have pores of several nanometers and the molecules passing the wall are not forming one mass of material with the materials inside the device. If the material is Bioresorbable then tissue can grow and replace the filling material resulting in a new space in the body filled with the new tissue. Using a bioresorbable filling material will result in tissue regeneration. For bone regeneration the filling material preferably is bone augmenting material which occupies a space in the body for several months. The filling material to allow expansion by inflation preferably is suspension of particles or cement or material with high viscosity. Most bone augmenting materials available today are particles or viscous gels or cements or combinations. The size of the holes can be determined by the size of the particles in the filling material or the degree of the viscosity of the filling material.

The pouch is filled one or more times every few days till the desired enlargement is reached. While the pouch expands it conducts tensile forces to the surrounding tissues which reacts in proliferation and enlargement. At the same time more biocompatible materials can be added. After the desired enlargement is reached the filling element can be pulled out if necessary. If the device is made from bioresorbable materials there is no need to take out the device. The end result is a new or enlarged compartment in the body filled with regenerated tissue and/or a biocompatible material.

The basic principle is to create a cavity into which tissue from a controlled direction is growing inside the cavity or to insert inside the body a biocompatible material to a predetermined location in a predetermined geometry and to allow contact between the tissue and the biocompatible material which preferably is bioactive. The filling material preferably is highly viscous, particulated or becomes rigid inside the body. The fact that there are holes of several dozens or several hundreds of microns allows the material to pass and to touch the surrounding tissue and to create one high viscous or rigid substance connecting the internal space created by the device and the tissue. This feature distinguishes the present invention from other inflatable devices that prevent direct contact between the internal space and the external space. There are devices that permit drug delivery through the envelop of the inflatable device but there is no inflatable device like the present devices that allow the immediate formation of a continuous mass of materials extending from the inside of the device to the tissue.

The insertion of the device can be through a small incision to a tunnel so all the process is done with almost no surgery.

There are many possible implementations of the device and method depending on several factors:
1. The place the device is inserted into.
2. The filling material.
3. The shape of the pouch.
4. The kind of filling element that is in use.
5. The kind of material the pouch is made of.

The device and method can be therefore used for selective regeneration of more or less specialized tissues, for example, membranes demarcating body cavities and/or separating different tissues and organs from each other, as well as, for selective regeneration of different tissues within the organs, or the organs themselves in relation to the surrounding tissues or nerves. Examples of membranes are the periosteum, the membranes of the brain and the peritoneal membrane; while examples of organs are the bones, bone cavities, liver, the throat, the ventricle, the kidney, the heart and the pancreas. Also, muscle tissue tendons, fat tissue, vessels, ducts, and tubes should be possible to regenerate with this device and method.

The device and method are particularly useful for plastic surgery, dental implantology, orthopedics and in cardiac surgery. In plastic surgery it can be used for soft tissue enlargement like lips and breasts and for facial bones enlargement. In dental implantology it can be used for horizontal and vertical augmentation of the alveolar ridge when the pouch is placed beneath the periosteum and for sinus augmentation when the pouch is placed beneath the Schneiderian membrane preceding the placement of dental implants. In orthopedics for fixating fractures and for minimal invasive delivering of bone regenerating materials to the gap between bone fragments.

The invention provides a method of correcting numerous bone abnormalities including bone tumors and cysts, avascular necrosis of the femoral head, tibial plateau fractures and compression fractures of the spine. The abnormality may be corrected by first accessing and boring into the damaged tissue or bone and reaming out the damaged and/or diseased area using any of the presently accepted procedures or the damaged area may be prepared by expanding a device within the damaged bone to compact cancellous bone. After removal and/or compaction of the damaged tissue the bone must be stabilized. In cases in which the bone is to be compacted, the methods and devices of this invention employ a catheter tube attached to an inflatable device. This device may be inflated with less fear of puncture and leakage of the inflation medium than thin walled rubber balloons. They may also be used over a Scribner balloon to protect the balloon from breakage and eventually seepage. The device additionally provide the surgeon with the advantage of safely skipping the first balloon inflation steps of Scribner and Scholten, by expanding the device through introduction of filling material, such as a bone repair medium thereby correcting the bony defect and deformity and stabilizing it in one step of the procedure The device preferably has one region that allows direct contact between the bone and the filling material to improve stabilization and another region that prevents direct contact and leakage of the filling material. As indicated above, the damaged bone may be removed by any conventional reamer. Examples of reamers are know and may be used. After the damaged bone or tissue has been removed, bone repair medium may then be inserted into the cavity. Alternatively, either a smaller than desired cavity may be formed into the bone to be enlarged by compaction or the cavity may be formed only by compaction through introduction of filling material into the device. In either case, the device may be positioned over the inflation balloon which is then inflated within the bone site to provide the degree of compaction required. The device may then be filled with filling material, such as bone repair medium while the balloon remains in place within the device. Alternatively, the balloon may be removed from the device prior to filling the bag.

Other objects and features of the present invention will become apparent in the following detailed description when taken in connection with the accompanying drawings which disclose one embodiment of the invention. It is to be understood that the drawings are designed for the purpose of illustration only and are not intended as a definition of the limits of the invention.

Thus, according to the teachings of the present invention there is provided, a method for expanding, stretching or displacing living tissue comprising: (a) inserting into the tissue an inflatable element made at least in part from bio-dissipative material; (b) introducing into the inflatable element a quantity of a biocompatible filling material so as to displace the tissue; and (c) leaving at least part of the inflatable element in place for a period sufficient to allow the bio-dissipative material to disperse.

According to a further feature of the present invention, the introducing is performed in a plurality of stages separated by at least a number of hours, each stage incrementally stretching the tissue.

According to a further feature of the present invention, the biocompatible filling material includes a bio-active material.

According to a further feature of the present invention, the biocompatible filling material includes material for promoting the growth of at least one type of tissue.

According to a further feature of the present invention, the inflatable element is located beneath the Schneiderian membrane of the maxillary sinus or of the nose.

According to a further feature of the present invention, the inserting is performed such that the inflatable element is located substantially at a bone-soft tissue interface, the biocompatible filling material including material for promoting the growth of bone such that, subsequent to dispersal of the inflatable element, the biocompatible filling material promotes extension of the bone beyond the initial bone-soft tissue interface.

According to a further feature of the present invention, the material for promoting the growth of bone includes at least one material selected from the group made up of: an autograft, an allograft, a xenograft, an alloplast, a cytokine, a hormone, a growth factor, a physiologically acceptable drug, a biological modifier, a protein, an antigen, a cell chemotaxis stimulator material, a material inducing osteogenesis, an osteoinduction material, and an osteoconduction material.

According to a further feature of the present invention, the inflatable element includes a guided bone regeneration membrane located so as to be adjacent to the soft tissue.

According to a further feature of the present invention, the inflatable element is configured to have a first region which exhibits a first mean time to dispersion and a second region which exhibits a second mean time to dispersion longer than the first mean time to dispersion.

According to a further feature of the present invention, the inflatable element is formed at least in part from a stretchable material.

According to a further feature of the present invention, the inflatable element is formed from more than one type of material.

According to a further feature of the present invention, the inflatable element is configured to have a first portion with a first stiffness and a second portion with a second stiffness differing from the first stiffness.

According to a further feature of the present invention, the inflatable element is formed at least in part from a material which serves as a selective barrier configured to allow at least a first material to traverse the barrier while preventing passage of at least a second material.

According to a further feature of the present invention, the inflatable element is formed at least in part from a self-expanding material.

According to a further feature of the present invention, the biocompatible filling material includes a self-expanding material.

According to a further feature of the present invention, the introducing is performed via a filling conduit partially inserted into the tissue.

According to a further feature of the present invention, the filling conduit is formed at least partially from non-bio-dissipative material.

According to a further feature of the present invention, the filling conduit includes a sealing means for sealing the filling conduit after the introducing of the biocompatible filling material.

According to a further feature of the present invention, disinfecting material is introduced into the filling conduit after the introducing of the biocompatible filling material.

According to a further feature of the present invention, the filling conduit is implemented as a bone implant.

According to a further feature of the present invention, the filling conduit is formed with at least one fixation feature.

According to a further feature of the present invention, the introducing is by temporarily puncturing the inflatable element with a needle inserted through the tissue, the inflatable element being configured to be self-sealing on removal of the needle.

According to a further feature of the present invention, prior to inserting the inflatable element, a tunnel is formed into the tissue for insertion of the inflatable element.

According to a further feature of the present invention, prior to inserting the inflatable element, a plurality of shallow, elongated incisions are formed in the tissue adjacent to the tunnel so as to facilitate stretching of the tissue.

According to a further feature of the present invention, the shallow elongated incisions are formed manually by moving an elongated tool with at least one laterally projecting blade in a reciprocating motion within the tunnel.

According to a further feature of the present invention, the elongated tool is configured to produce incisions of depth no greater than about 2 mm.

According to a further feature of the present invention, the elongated tool is configured to produce incisions of depth between about 0.1 mm and about 1 mm.

According to a further feature of the present invention, the inflatable element is configured to apply outward force on a substantially cylindrical living tissue without completely obstructing a flow path which passes within the substantially cylindrical living tissue.

According to a further feature of the present invention, the inflatable element is configured as a double-walled sleeve.

There is also provided according to the teachings of the present invention, a device for expanding, stretching or displacing living tissue comprising: (a) an inflatable element for insertion into the tissue, the inflatable element being made at least in part from bio-dissipative material; and (b) means for introducing into the inflatable element a quantity of a biocompatible filling material so as to displace the tissue.

According to a further feature of the present invention, the inflatable element is configured to have a first region which exhibits a first mean time to dispersion and a second region which exhibits a second mean time to dispersion longer than the first mean time to dispersion.

According to a further feature of the present invention, the inflatable element includes a guided bone regeneration membrane.

According to a further feature of the present invention, the inflatable element is formed from a plurality of types of material.

According to a further feature of the present invention, the inflatable element is configured to have a first portion with a first stiffness and a second portion with a second stiffness differing from the first stiffness.

According to a further feature of the present invention, the inflatable element is formed at least in part from a material which serves as a selective barrier configured to allow at least a first material to traverse the barrier while preventing passage of at least a second material.

According to a further feature of the present invention, the inflatable element is formed at least in part from a self-expanding material.

According to a further feature of the present invention, the inflatable element is formed at least in part from a stretchable material.

According to a further feature of the present invention, the means for inflating includes a filling conduit configured for inserting into the tissue so as to be accessible from outside the tissue, the filling conduit being formed with at least one fixation feature configured to allow fixation of the conduit relative to the tissue.

According to a further feature of the present invention, the filling conduit is formed at least in part from non-bio-dissipative material.

According to a further feature of the present invention, the filling conduit includes a sealing means.

According to a further feature of the present invention, the filling conduit includes a chamber for receiving disinfectant material.

According to a further feature of the present invention, the filling conduit is implemented as a bone implant.

According to a further feature of the present invention, the means for introducing includes a hollow needle configured to pierce part of the inflatable element for filling, the inflatable element being configured to reseal itself after withdrawal of the needle.

According to a further feature of the present invention, the inflatable element is configured to apply outward force on a substantially cylindrical living tissue without completely obstructing a flow path which passes within the substantially cylindrical living tissue.

According to a further feature of the present invention, the inflatable element is configured as a double-walled sleeve.

There is also provided according to the teachings of the present invention, an elongated tool for forming shallow elongated incisions in living tissue adjacent to a tunnel formed through the tissue so as to facilitate stretching of the tissue, the tool comprising: (a) a handle; (b) an elongated shaft associated with the handle, the elongated shaft having a direction of elongation, a maximum transverse dimension measured perpendicular to the direction of elongation and a length measured parallel to the direction of elongation, wherein the maximum transverse dimension is at least about 3 mm and wherein the length is at least five times the maximum transverse dimension; and (c) at least one blade projecting from the elongated shaft and configured to form incisions of depth no greater than 2 mm in adjacent tissue when the tool is inserted within the tunnel and moved parallel to the direction of elongation.

According to a further feature of the present invention, the length is at least about ten times the maximum transverse dimension.

According to a further feature of the present invention, the maximum transverse dimension is between about 5 mm and about 10 mm.

According to a further feature of the present invention, the at least one blade is configured to form incisions of depth between about 0.1 mm and about 1 mm.

There is also provided according to the teachings of the present invention a method for expanding, stretching, displacing or fixating living tissue comprising: (a) inserting into the tissue an inflatable element, the inflatable element includes at least one not-sealed region being configured after being filled with a biocompatible material to enable contact between the tissue and the biocompatible material; and (b) introducing into the inflatable element a quantity of a biocompatible filling material, the introducing being performed in a plurality of stages separated by at least a number of hours.

Thus, according to the teachings of the present invention there is provided, a method for expanding, stretching, displacing, fixating or treating living tissue comprising:

inserting into the tissue an expandable element, the expandable element includes at least one soft pliable region, the expandable element being configured to allow filling with a biocompatible material so as to enable immediate direct contact between the tissue and the biocompatible filling material so as to create a continues mass of the biocompatible filling material connecting the tissue with the space created by the expandable device; and expanding the expandable element.

According to a further feature of the present invention the expanding being performed in a plurality of stages separated by at least a number of hours.

According to a further feature of the present invention the biocompatible filling material is highly viscous and configured to occupy the space for at least several months.

According to a further feature of the present invention the biocompatible filling material includes rigid particles and configured to occupy the space for at least several months.

According to a further feature of the present invention the expanding being performed in a plurality of stages separated by at least a number of hours.

According to a further feature of the present invention the method includes insertion of a biocompatible filling material through the expandable element.

According to a further feature of the present invention the insertion of the biocompatible filling material is expanding the expandable element.

According to a further feature of the present invention the expandable element is made at least in part from bio-dissipative material.

According to a further feature of the present invention the expandable element has one region which prevents contact between the said tissue and said biocompatible filling material.

According to a further feature of the present invention the introducing is displacing the tissue.

According to a further feature of the present invention the expandable element has a first region with a first resistance to passage of a given material and a second region with a second resistance to passage of the given material, the second resistance being less than the first resistance.

According to a further feature of the present invention the given material includes cells and blood vessels.

According to a further feature of the present invention the biocompatible filling material includes a bio-active material.

According to a further feature of the present invention the inserting is performed such that the expandable element is located substantially at a bone-soft tissue interface, the biocompatible filling material including material for promoting the growth of bone such that, subsequent to the contact of the biocompatible filling material with the tissue the material for promoting the growth of bone promotes extension of the bone beyond the initial bone-soft tissue interface.

According to a further feature of the present invention the expandable element is configured to have a first region which exhibits a first mean time to dispersion and a second region which exhibits a second mean time to dispersion longer than the first mean time to dispersion.

According to a further feature of the present invention the introducing is performed via a filling conduit partially inserted into the tissue.

According to a further feature of the present invention the filling conduit is implemented as a bone implant.

According to a further feature of the present invention the expandable element is configured to take a specific shape as the expandable element is filled and to resist changes in the shape of the expandable element as a result of forces coming from outside the expandable element.

According to a further feature of the present invention the expandable element is configured to grow in a telescopic pattern.

According to a further feature of the present invention the expandable element includes a component assisting in the enlargement of the expandable element.

According to a further feature of the present invention the expandable element includes at least one region having a first stiffness and a second region having a second stiffness less than the first stiffness so as to define a direction of expansion of the expandable element.

According to a further feature of the present invention the expandable element is closed by being attached to at least one surface of the tissue such that the expandable element becomes inflatable after being attached to the tissue.

According to a further feature of the present invention the expandable element is placed beneath the gums.

According to a further feature of the present invention the expandable element includes a rigid element facing the gums, the rigid element being attached to a non rigid element configured so as to grow in a telescopic pattern, the rigid element includes at least one tube being configured to protrude through the gums to the oral cavity, the tube being configured to be sealed with a sealing component.

According to a further feature of the present invention the expandable element includes mechanical mechanism configured to allow displacement of the rigid element from the bone so as to displace the gums.

According to a further feature of the present invention the mechanical mechanism is connected to a dental implant configured to support a dental prosthesis.

According to a further feature of the present invention the mechanical mechanism includes a stabilizing component to prevent micro-motion of the rigid element.

According to a further feature of the present invention the non rigid element is a guided bone regeneration membrane.

According to a further feature of the present invention the expandable element includes at least one elevating screw configured to allow displacement of the rigid element from the bone so as to displace the gums.

According to a further feature of the present invention the expandable element includes at least one elevating nut configured to be threaded on the elevating screw, the elevating nut being configured to be accessible through the tube, the elevating nut being configured to touch the rigid element so as turning the elevating nut results in displacement of the rigid element.

According to a further feature of the present invention the elevating screw is hollow and perforated so as to allow insertion of bone augmenting material through the upper region of the elevating screw inside the space of the expandable element, the upper region of the elevating screw being configured to be accessible through the tube.

According to a further feature of the present invention the elevating screw is a dental implant configured to support a dental prosthesis.

According to a further feature of the present invention the tube is configured to be detached from the rigid element leaving a hole in the rigid element, the hole being wide enough to allow replacement of the elevating screw with a bone implant through the hole, the bone implant being connected to the rigid element by a stabilizing element, the stabilizing element includes one region configured to be threaded to the internal threads of the bone implant and a second region configured to be threaded to threads in the rigid element around the hole, the stabilizing element is configured to seal the hole.

According to a further feature of the present invention the expandable element is inserted inside the breast and said biocompatible filling material is fat cells.

According to a further feature of the present invention the fat cell are sucked from another region in the body.

According to a further feature of the present invention the expandable element being configured after being filled with a setting biocompatible filling material to fixate the tissue as the setting biocompatible filling material sets; and introducing into the expandable element a quantity of a setting biocompatible filling material.

There is also provided according to the teachings of the present invention a method for expanding, stretching, displacing or fixating living tissue comprising: (a) inserting into the tissue an inflatable element made having a first region which is perforated so as to allow penetration of cells and blood vessels and a second region which is resistant to ingrowth of tissue; and (b) introducing into the inflatable element a quantity of a biocompatible filling material so as to displace the tissue.

According to a further feature of the present invention the inflatable element is made at least in part from bio-dissipative material.

According to a further feature of the present invention the introducing is performed in a plurality of stages separated by at least a number of hours, each stage incrementally stretching the tissue.

According to a further feature of the present invention the biocompatible filling material includes a bio-active material.

According to a further feature of the present invention the biocompatible filling material includes material for promoting the growth of at least one type of tissue.

According to a further feature of the present invention the inflatable element is located beneath the Schneiderian membrane of the maxillary sinus or of the nose.

According to a further feature of the present invention the inflatable element having one region that can be detached from the inflatable element and taken out of the tissue after filling of the inflatable element so as to enable direct contact between the biocompatible filling material and the tissue.

There is also provided according to the teachings of the present invention method for expanding, stretching, displacing or fixating living tissue comprising: (a) inserting into the tissue an inflatable element, the inflatable element being configured after being filled with a setting biocompatible filling material to fixate the tissue as the setting biocompatible filling material sets; and (b) introducing into the inflatable element a quantity of a setting biocompatible filling material.

According to a further feature of the present invention the inflatable element is made at least in part from bio-dissipative material.

According to a further feature of the present invention the inflatable element has a first region with a first resistance to passage of a given material and a second region with a second resistance to passage of the given material less than the first resistance.

According to a further feature of the present invention the inflatable element is configured to take a specific shape as the inflatable element is filled and to resist changes in the shape of the inflatable element as a result of forces coming from outside the inflatable element.

According to a further feature of the present invention the inflatable element is configured so as to enable contact between the tissue and the setting biocompatible filling material.

According to a further feature of the present invention the inflatable element is configured to fix two tissue fragments in given spatial relation.

According to a further feature of the present invention wherein the inflatable element has a first region which is perforated to allow not damaging leakage of the biocompatible filling material and a second region which is resistant to leakage of the biocompatible filling material.

According to a further feature of the present invention the first region is facing bone and the second region is facing other tissues.

According to a further feature of the present invention the inflatable element is inserted into a space inside bone.

According to a further feature of the present invention the inflatable element is inserted between two bone fragments.

According to a further feature of the present invention the inflatable element is inserted into a crushed vertebra.

According to a further feature of the present invention the introducing is displacing the tissue.

According to a further feature of the present invention the introducing is displacing the fragments of the crushed vertebra.

There is also provided according to the teachings of the present invention a device for expanding, stretching, displacing or fixating living tissue comprising: (a) an inflatable element for insertion into the tissue, the inflatable element includes at least one not-sealed region being configured after being filled with a biocompatible material to enable contact between the tissue and the biocompatible material; and (b) means for introducing configured to be accessible from outside the tissue and to allow filling of the inflatable element several times, the means for introducing including sealing means configured to seal the means for introducing.

There is also provided according to the teachings of the present invention a device for expanding, stretching, displacing or fixating living tissue comprising:

an expandable element for insertion into the tissue, the expandable element includes at least one soft pliable region, the expandable element being configured to allow filling with a biocompatible material so as to enable immediate direct contact between the tissue and the biocompatible filling material so as to create a continuous mass of the biocompatible filling material connecting the tissue with the space created by the expandable device.

According to a further feature of the present invention the expandable element has means for introducing configured to be accessible from outside the tissue and to allow filling of the expandable element several times, the means for introducing including sealing means configured to seal the means for introducing.

According to a further feature of the present invention the expandable element is made at least in part from bio-dissipative material.

According to a further feature of the present invention the expandable element has a first region with a first resistance to passage of a given material and a second region with a second resistance to passage of the given material less than the first resistance.

According to a further feature of the present invention the expandable element is configured to take a specific shape as the expandable element is filled and to prevent changes in the shape of the expandable element as a result of forces coming from outside the expandable element.

According to a further feature of the present invention the expandable element is configured to grow in a telescopic pattern.

According to a further feature of the present invention the expandable element includes a component assisting in the enlargement of the expandable element.

According to a further feature of the present invention the expandable element is configured to be closed by being attached to at least one surface of the tissue such that the expandable element becomes inflatable after being attached to the tissue.

According to a further feature of the present invention the expandable element is configured to have a first region which exhibits a first mean time to dispersion and a second region which exhibits a second mean time to dispersion longer than the first mean time to dispersion.

According to a further feature of the present invention the means for introducing is a filling conduit.

According to a further feature of the present invention the filling conduit is implemented as a bone implant.

According to a further feature of the present invention the expandable element includes at least one region having a first stiffness and a second region having a second stiffness less than the first stiffness so as to define a direction of expansion of the expandable element.

According to a further feature of the present invention the expandable element is formed at least in part from a material which serves as a selective barrier configured to allow at least a first material to traverse the barrier while preventing passage of at least a second material.

According to a further feature of the present invention the expandable element is formed with at least one fixation feature.

According to a further feature of the present invention the filling conduit includes a chamber for receiving disinfectant material.

According to a further feature of the present invention the expandable element includes a rigid element, the rigid element being attached to a non rigid element configured so as to grow in a telescopic pattern, the rigid element includes at least one tube being configured to protrude through the gums to the oral cavity, the tube being configured to be sealed with a sealing component.

According to a further feature of the present invention the expandable element includes mechanical mechanism configured to allow displacement of the rigid element.

According to a further feature of the present invention the mechanical mechanism includes a stabilizing component to prevent micro-motion of the rigid element.

According to a further feature of the present invention the mechanical mechanism is configured to be connected to a dental implant configured to support a dental prosthesis.

According to a further feature of the present invention the non rigid element is a guided bone regeneration membrane.

According to a further feature of the present invention the expandable element includes at least one elevating screw configured to allow displacement of the rigid element.

According to a further feature of the present invention the expandable element includes at least one elevating nut configured to be threaded on the elevating screw, the elevating nut being configured to be accessible through the tube, the elevating nut being configured to touch the rigid element so as turning the elevating nut results in displacement of the rigid element.

According to a further feature of the present invention the elevating screw is hollow and perforated so as to allow insertion of bone augmenting material through the upper region of the elevating screw inside the space of the expandable element, the upper region of the elevating screw being configured to be accessible through the tube.

According to a further feature of the present invention the elevating screw is a dental implant configured to support a dental prosthesis.

According to a further feature of the present invention the tube is configured to be detached from the rigid element leaving a hole in the rigid element, the hole being wide enough to allow replacement of the elevating screw with a bone implant through the hole, the bone implant being connected to the rigid element by a stabilizing element, the stabilizing element includes one region configured to be threaded to the internal threads of the bone implant and a second region configured to be threaded to threads in the rigid element around the hole, the stabilizing element is configured to seal the hole.

There is also provided according to the teachings of the present invention a device for expanding, stretching, displacing or fixating living tissue comprising: an inflatable element configured after being filled with a setting biocompatible filling material to fixate the tissue as the setting biocompatible filling material sets; and means for introducing into the inflatable element a quantity of the setting biocompatible filling material.

According to a further feature of the present invention the inflatable element is made at least in part from bio-dissipative material.

According to a further feature of the present invention the inflatable element having a first region with a first resistance to passage of a given material and a second region with a second resistance to passage of the given material less than the first resistance.

According to a further feature of the present invention the inflatable element is configured to take a specific shape as the inflatable element is filled and to resist changes in the shape of the inflatable element as a result of forces coming from outside the inflatable element.

According to a further feature of the present invention the inflatable element is configured so as to enable contact between the tissue and the setting biocompatible filling material.

According to a further feature of the present invention wherein the inflatable element is configured to fix two tissue fragments in given spatial relation.

According to a further feature of the present invention wherein the inflatable element has a first region which is perforated to allow not damaging leakage of the setting biocompatible filling material and a second region which is resistant to leakage of the setting biocompatible filling material.

BRIEF DESCRIPTION OF THE DRAWINGS

The invention is herein described, by way of example only, with reference to the accompanying drawings, wherein:

FIG. 1 is a perspective view illustrating the novel device used in accordance with the invention to receive and contain bone augmentation material. In this preferred embodiment the filling element is a cannula.

FIG. 2 is a perspective view illustrating the device of FIG. 1 After it was filled with bone augmenting material.

FIG. 3 is a bottom view illustrating the device of FIG. 2.

FIG. 4 is a sectional view of the device in a telescopic configuration.

FIG. 10A is a sectional view illustrating the elevating abutment, which is part of the elevating mechanism.

FIG. 10B is side view of the plate and the tubes.

FIG. 10C is a sectional view of the dental implant.

FIG. 10D is a sectional view of the hollow screw, which is part of the elevating mechanism.

FIG. 10E is a sectional view of the nut, which is part of the elevating mechanism.

FIG. 10F is a sectional view of the fixating screw, which is part of the elevating mechanism.

FIG. 11 is a sectional view of the plate of FIG. 10B in the bucco-lingual aspect.

FIG. 12 is a perspective view of the plate of FIG. 10B.

FIG. 13A is a side view of the device after placement subperiostealy.

FIG. 13B is a side view of the device of FIG. 13A at the end of the periosteal distraction.

FIG. 13C is a side view of the device of FIG. 13A after replacement of the elevating mechanism with the stabilizing mechanism.

DESCRIPTION OF THE PREFERRED EMBODIMENTS

Figure 5A:
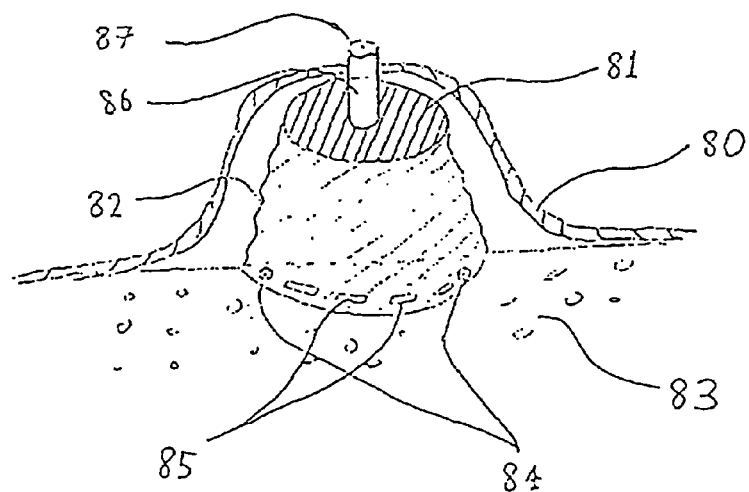
FIG. 5A is a perspective view illustrating the novel device used in accordance with the invention made from a rigid plate connected to a flexible sheet.

As mentioned further above there are many implementations of the invention in different tissues and organs. The following description will focus on embodiments in two fields in order to understand the principles of the device and method. The first is bone augmentation in the jaws the second is fixating bone fragments. The same principles should be used in other tissues and organs.

Before turning to the features of the present invention in more detail, it will be useful to clarify certain terminology as will be used herein in the description and claims. Specifically, it should be noted that the present invention is useful in a wide range of applications in which living tissue is to be expanded, stretched, fixated or displaced. The term "living tissue" is used herein to refer to any living tissue including, but not limited to, an organ, tube, vessel, cavity, bone cavity or membrane, and interfaces between any two or more of the above. Where used within a single type of tissue, the typical application of the present invention is for expanding the tissue. When used at a tissue interface, the invention is typically used to displace one of the types of tissue, in many cases for the purpose of expanding/extending the other tissue. The invention may also be used to increase the inner dimensions of tubes, vessels cavities or bone cavities within the body.

In another matter of terminology, it is noted that a large number of different types of materials are known which may be inserted within the body during a surgical procedure and which later dissipate, thereby avoiding the need for a separate surgical procedure for their removal. Such materials are properly referred to, depending upon the mechanism by which the material dissipates, as "bioresorbable", "bioabsorbable" or "biodegradable". Despite the differences between these different classes of materials, the aforementioned terminology is widely used interchangeably by medical professionals. Accordingly, and for conciseness of presentation, only one of these terms will generally be used in the following description, without implying the exclusion of the other classes of materials. Additionally, the phrase "bio-dissipative material" is used herein in the description and claims to refer generically to any and all materials which dissipate without requiring surgical removal, independent of which mechanisms such as dissolution, degradation, absorption and excretion take place. The actual choice of which type of materials to use may readily be made by one ordinarily skilled in the art, and is not generally essential to the present invention.

Finally with respect to terminology, reference will be made to a biocompatible filling material used to fill the inflatable elements of the present invention. It should be noted that this filling material may assume a wide range of compositions and consistencies, so long as the biocompatible material may be forced into the inflatable element. Thus, possible consistencies for the filling material include, but are not limited to, consistencies described as watery, viscous, gelatinous, moldable, waxen, particulate, and suspensions or mixtures combining any of the above.

Turning now in detail to the drawings, which depict the presently preferred embodiments of the invention for the purpose of illustrating the practice thereof and not by way of limitation of the scope of the invention, and in which like reference characters refer to corresponding elements throughout the several views.

FIG. 1, illustrates the novel device embodying the present invention for use in bone reconstruction and, in particular, for augmentation of atrophic alveolar ridges. The device is composed of a pouch 5. The pouch can be made from autograft, allograft, xenograft and alloplast and combination thereof. The pouch is made from a biocompatible material. Preferably, the pouch is made at least in part from resorbable materials to prevent a chronic foreign body reaction like: conventionally available polyglycolic acid (PGA) mesh, a high-molecular-weight linear polymer made by the ring opening polymerization of the purified glycolide monomer, although other suitable materials might be used e.g. polyglactin 910, i.e. polyglycolide co-galactide. In addition, collagen or PDS (another absorbable suture material) or cellulose might possibly also be used as a pouch material. The pouch can be perforated all over to allow tissue ingrowth and some degree of leakage of the filling material. The size of pores depend on the filling material, preferably the size of the pores are several hundreds of microns and even several millimeters. The pouch preferably has a porous region preferably towards the bone to allow bone tissue ingrowth and preferably has a region that blocks epithelial tissue ingrowth. The pouch preferably allows some filling material to get out of the pouch under pressure through the perforated region. Expanding a perforated pouch can be done with particulated filling material. Most bone augmenting materials are available as particles in the size of 200-2000 microns. To allow easy insertion preferably the particles are mixed with a solution like saline, blood or biocompatible gels like cellulose, glycerol and hydrogel. If the size of the pores in the pouch are 1.5-5 times greater than the particles size the pouch can be inflated. Some particles can get out of the pouch but no massive leakage can occur. Preferably the pores are 3 times the particles size. This feature allows inflation of the pouch with minor leakage and immediate direct contact between the filling material and the bone with no danger for massive or damaging leakage. The perforated pouch can be also inflated using a high viscous gel like Dinagraft which is gelatinous allograft bone augmenting material or with bone cements like PMMA. The end result is one continuous mass of the filling material which is rigid or highly viscous connecting the tissue and the internal space of the device for at least several months.

The pouch 5 is connected to a conduit in the shape of a cannula 6. The conduit can be also catheter, valve, bone implant, syringe and combination thereof. Bone implant can be hollow bone implant, slotted bone implant, threaded implant, cylinder implant, smooth surface implant, titanium plasma sprayed implant, hydroxyapatite coated implant, acid etched surface implant, sand blasted surface implant, S.L.A. surface implant, ceramic implant, zirconium implant and any combination thereof.

The conduit is made of a biocompatible material and can be made from more than one type of material bioresorbable or non-bioresorbable. Preferably the cannula is made of commercially pure titanium or titanium alloy used in the dental implant industry. The cannula is connected to the pouch in one side and in the other side it can be filled and closed with a screw 7 as a sealing component. Sealing components can be also a valve, a clamping element, a knot and combination thereof The conduit can have variable shapes, dimensions, cross section and elasticity The cannula 6 has preferably fixating components in order to prevent the cannula from moving, get out and cause uncomfortable filling to the patient. The a fixation component can be selected from the group consisting of hook, hole for sutures, slot, thread, bulge, screw, change in dimension, irregularity and any combination thereof.

In this preferred embodiment there are three fixating components. One fixating component is a slot 8 that is near the pouch and inserted into the body. After the tissue heals around the slot it prevents the cannula from getting out easily. The other two fixating components are holes for sutures 9 that are near the sealing screw 7 and not inserted into the body. After the insertion of the device the pouch can be filled with bone augmenting material causing the wrinkled and compressed pouch 5 to expands and become a filled pouch 10 in FIG. 2.

The pouch can be made of more than one type of material. Preferably the pouch is composed of two Types of resorbable materials. One type that is rapidly resorbed and allows bone ingrowth and the second type that is slowly resorbed and prevents the ingrowth of epithelial tissue. It can also be made as illustrated in FIG. 3 of one type that is perforated 11 allowing contact between the filling material and the bone and the second type 12 preventing direct contact and leakage of the filling material. The perforated region preferably has pores that allows the filling material to get outside the pouch to wet the external surface of the pouch but prevents leakage of the filling material. The size of the pores are dependent on the filling material. For PMMA cement the pore size are in the range of 0.05-0.5 mm depending on the viscosity of the cement. When inserting the pouch the rapidly resorbed material or the perforated material 11 should face the bone. The perforated region can have one or several macro holes of several dozens of microns or to have one or several big holes of several millimeters. The end result is a continuous rigid mass of cement connected to the tissue and going inside the device.

The slowly resorbed material 12 can be also not resorbable material like ePTFE if in this case the gums are going to be open when placing the dental implants and then the not resorbable material can be taken out.

The pouch can include also self expanding components. Materials include, either alone or in combination, metals or metal alloys, polymers, carbon and ceramics. Exemplary metallic members include stainless steel, titanium, tantalum, shape-memory materials such as nickel-titanium alloy (NiTi) (Compounds using NiTi are manufactured under the marks NITINOL™ and ELASTINITE™ and are available from several sources), Elgiloy (trade name) and NP35N (trade designation), which can provide desired degree of springiness, malleability and/or response to temperature changes. Exemplary polymers include polyurethanes, silicon rubbers, polyether, sulfones, fluoroelastomers, polyimides, polycarbonates, polyethylens, polylactic acid, polyglycolic acid, polyacrylates, and the like and combinations and copolymers thereof which provide a variety of abilities to bioabsorb or biodegrade or to be totally inert. The pouch can include springs and coils that are compressed before insertion and can include stretchable and elastic materials for example polyurethanes like polycarbonate urethane.

In another preferred embodiment the pouch can include materials with different degree of stiffness. The material facing the bone can be less stiff than the material facing the gums.

The combination of several regions with different degree of stiffness can influence the direction of enlargement of the pouch and also the shape of the filled pouch. The pouch can have variable shapes and volumes according to the use. For example to reconstruct the entire jaw the pouch will be elongated in C-shape and filling element will be attached in the middle.

In another preferred embodiment the inflatable element can be configured to expand in a pre designed direction and take a specific shape as it is being filled. For example the inflatable element can be designed in a telescopic configuration as illustrated if FIG. 4. The inflatable element can be made from a stiff small container 61, that its open side is facing the bone 62 located inside a larger stiff container 63 that its open side is facing the gums 64, between the walls of the containers one 65 or several small walls can be also. The base 66 of the bigger container that is touching the bone is preferably made from a stiff bioresorbable material like polylactic acid, the rest of the inflatable element can be made also from bioresorbable materials or from non-resorbable biocompatible materials like titanium. The base preferably is perforated to allow the filling material to touch the bone. The diameter of the container and the walls in the region facing the bone is larger then the diameter in the opposite side. Therefore when pushing the small container upwards towards the gums till it's lower region will reach the upper region of the adjacent wall it will pull the adjacent wall upwards. Each wall in this way will pull the next wall resulting in a higher and a bigger compartment with a pre designed shape.

In another preferred embodiment the device of FIG. 4 can be without a base and the bone becomes the base of the device. In this embodiment the device becomes inflatable after placing over the bone and fixating to the bone. The device can be made from non resorbable materials like titanium.

In another preferred embodiment the perforated pouch can be covered by a rigid structure with a pre designed form so when the pouch is filled it will take the form of the rigid structure. In another embodiment the rigid structure can be place over the gums so when the pouch beneath the gums is filled the pouch and the gums will take the shape of the rigid structure.

In another preferred embodiment the pouch also includes a selective barrier that permits transfer of some cells and materials and prevents the transfer of other cells and materials. Therefore allowing bone forming cells and blood to get inside the pouch and block the entrance of connective tissue cells. This barrier can also permit the release of medication mixed with the filling material without letting the filling material to leak. This barrier should be adopted for its specific use for example to have little holes, sized according to the medicine to be released.

In another preferred embodiment the inflatable element can include a mechanical component that assists in the enlargement of the device. The mechanical component can include a screw that its activation enlarges the device. After the device was enlarged a biocompatible material like bone augmenting material can be inserted into the space created by enlarging the device. The tissue is displaced by activating the mechanical component and the filling of the device plays a minor role in the displacement of the tissue or no role at all. These embodiments utilizing the mechanical component are especially useful for vertical ridge augmentation. There are several options of using this principle. In one embodiment the device of FIG. 4 includes an elevating screw that is entering through the upper region of the small container 61 and engages threads in the upper region of the container. The screw touches the base of the container 66. The screw protrudes through the gums so when the screw is activated the small container is displaced and the device is enlarged. The space can be filled with a bone augmenting material by using a filling conduit. The filling conduit can protrude from the upper region of the device. In this embodiment the upper region has two protrusions one the screw and the other the filling conduit. In a preferred embodiment the screw can be also the filling conduit. In this preferred embodiment the screw is hollow and perforated and configured to allow insertion of bone augmenting material. In a preferred embodiment the screw is turned and filling is done simultaneously by using a special syringe that can also rotate the screw. In a preferred embodiment the screw is a bone implant. In all the cases described in this application when a screw is mentioned it includes also the possibility of being a bone implant or a dental implant. If the screw is a bone implant it has significant advantage over a regular screw that there is no need for later insertion of bone implants therefore saving for the patients another surgical procedure and the time of the treatment is reduced. In another preferred embodiment the device has no base as mentioned before and the filling material is touching the bone. In this embodiment the elevating screw is touching the bone. In this embodiment drilling a hole in the bone for the tip of the elevating screw is recommended. In another embodiment a small base implant can be inserted to the bone. This base implant has an internal hole configured to stabilize the tip of the elevating screw. In this embodiment the elevating screw doesn't touch the bone, therefore activating the screw cause no pain to the patient. In this embodiment as mentioned before the screw can be a bone implant or dental implant and also hollow and also perforated and function also as the filling conduit.

Figure 5B:
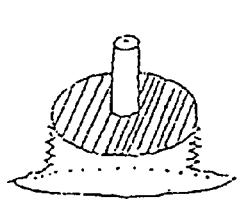
FIG. 5B is a perspective view of the device of FIG. 5A when the sheet is folded vertically.
Figure 5C:
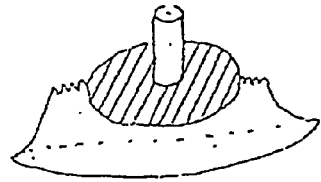
FIG. 5C is a perspective view of the device of FIG. 5A when the sheet is folded horizontally.

In another preferred embodiment illustrated in FIG. 5A the device is made from two parts the upper part facing the gums 80 is a plate 81 made from a rigid material like titanium or a rigid bio-dissipative material and a membrane 82 that is attached around the plate 81. The membrane 82 preferably forms a substantially conical structure. The small diameter of the cone is attached to the plate 81 and the large diameter is configured to be attached to the bone 83. The membrane 82 can be attached to bone by little screws or bone tacks 84. The membrane can be perforated at the edge near the bone so after placement of the device and suturing the periosteum, the periosteum adheres to the bone through the holes 85 in the membrane so the membrane 82 becomes attached to the bone 83. The membrane 82 is preferably folded at the beginning so the rigid plate 81 is placed close to the bone. When the device is enlarged the folds are opened and the plate 81 is displaced from the bone. The enlargement can be by filling the device though a tube 86 that is connected to the plate 81. The tube has preferably a sealing screw 87. The enlargement can be by using an elevating screw as described above. The use of a membrane 82 as the telescopic element instead of a rigid structure as described in FIG. 4 enables to fit easily the device to different architectures of bones. The membrane can be a guided bone regeneration membrane and can be bio-dissipative. The folds of the membrane can be in the vertical dimension as in FIG. 5B or in the horizontal dimension as in FIG. 5C and in any configuration that allows for enlargement of the device. Another advantage of the use of a membrane is that the elevating screw allows vertical enlargement and displacement of the gums and the filling of the device allows for horizontal enlargement and displacement of the gums.

The meaning of the term rigid all over the application is that the plate is more rigid than rubber or cloth like material. Preferably even more rigid than the periosteal tissue therefore the shape of the periosteal tissue is dictated by the shape of the rigid plate. The plate can be completely rigid like metal or semi rigid like plastic.

Another important feature of the device is to prevent micro-motion of the plate. In case of distraction osteogenesis and fracture healing micro-motion is known to accelerate the healing. In the embodiments of the present invention micro-motion of the plate will create fibrocapsular reaction and will prevent bone regeneration. The devices known for distraction osteogenesis which are based on screws can not prevent micro-motion. The micro-motion preferably should be less than 50 micrometers. The following devices must include a stabilizing element to prevent micro-motion. The distraction mechanism by itself as it is in osteogenesis distractors can not prevent micro-motion. This innovative feature is critical for the success of the device.

Figure 7:
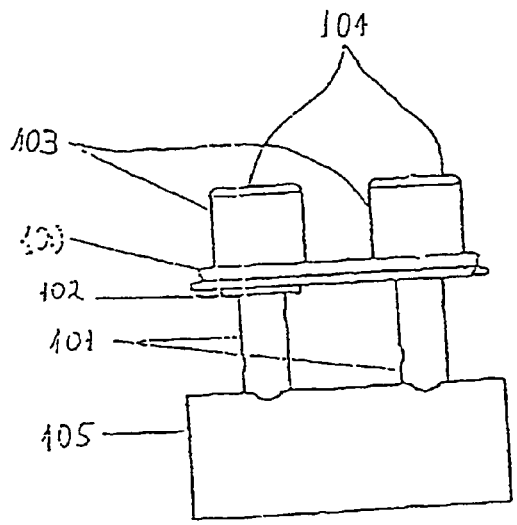
FIG. 7 is a sectional view of the device of FIG. 6 to illustrate the use of two elevating screws and nuts.
Figure 6:
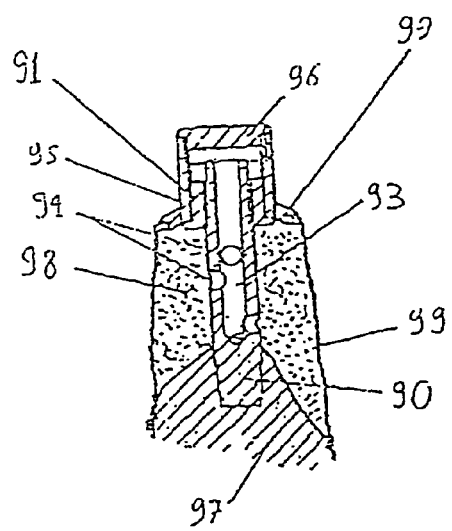
FIG. 6 is a sectional view of the device of FIG. 5A that includes a perforated hollow screw and an elevating nut to displace the plate from the bone.

Another preferred embodiment is illustrated in FIG. 6. FIG. 6 is a sectional view of the device after placement on the bone 97 and being filled with bone augmenting material 98. The elevating screw 90 is fixated to the bone 97 and an elevating nut 91 is threaded on the elevating screw. The elevating nut is configured to displace the upper plate 92 and consequently unfold the folded membrane 99 that is attached to the plate as described in FIG. 5. In this embodiment the screw 90 helps also in stabilizing the plate 92 and in controlling the direction of enlargement. The screw 90 as mentioned can be hollow 93 and perforated 94 and can be a bone implant or a dental implant. In the embodiments that the screw is configured to be the bone implant, it is recommended that the screw will not be in direct contact with the oral environment, in order to keep the properties of the surface of the bone implant. In these embodiments the plate can include a tube 95 that can be sealed with a sealing cup 96. The elevating screw 90 is placed in the space of the tube 95 and activating the nut 91 is done through the tube 95. Filling the device can be through the screw 90 if it is hollow or through another opening in the plate. In another preferred embodiment illustrated in FIG. 7 a device like the device of FIG. 6 has more then one elevating screw. FIG. 7 is a side view of the device after removal of the membrane. The plate 100 is like the plate 92 of FIG. 6 but is more elongated. There are two elevating screws 101, two nuts (one is illustrated 102), two tubes 103, two sealing cups 104. This embodiment is recommended for the augmentation of edentulous ridge 105. The use of more then one elevating screw 101 improves the stabilization of the device and prevents the rotation of the upper plate 100 when activating the elevating nuts 102. It is recommended that the tubes 103 are made of titanium. The screws 101 are preferably hollow and perforated. The screws are inserted by using a parallelism guide. After the screws 101 are inserted the nuts 102 are placed over the screws and threaded to be adjacent the bone 105. Then the plate 100 is placed over the screws 101 and nuts 102 and the folded membrane is attached to the bone 105. The tubes 103 can be sealed by using sealing cups 104. The sealing cups 104 can be threaded to the tubes 103 if the tubes 103 have threads in their upper region. Preferably the sealing cups 104 are threaded to the elevating screws 101 so they can function as a stabilizing element to prevent micro-motion of the plate. At the beginning the sealing cups 104 are high and should be replaced with lower cups as the device is enlarged. It is recommended to enlarge vertically the device at a rate of 1 mm per day. In each enlargement filling of the device with bone augmenting material can be done. It can be done simultaneously or the filling is done after the mechanical enlargement or before the mechanical enlargement. The filling preferably can be done after the plate is distracted to the final position so there is only one procedure of filling. The enlargement of the devices described here and above can be done in several steps or continuously over a period of several hours or days. The continuous manner can include a pump for continuous filling of the device and a mechanical or electrical component that exerts forces for a long period of time. After the device has reached its final dimension and it is filled with bone augmenting material, it is possible to add bio-active materials into the device even several weeks and months later. Bio-active material can be Bone Morphogenic Proteins (B.M.P) that accelerates the regeneration of bone or can be antibiotics in case of infection.

In another preferred embodiment the screws are regular dental implants that are not perforated and the filling is done through another opening or through the gap between the tube and the elevating screw. In this embodiment the tube is the filling conduit. The plate can be elevated about 1 mm above the regular dental implants to allow filling with the bone augmenting material in the gap between the dental implants and the plate.

Figure 8:
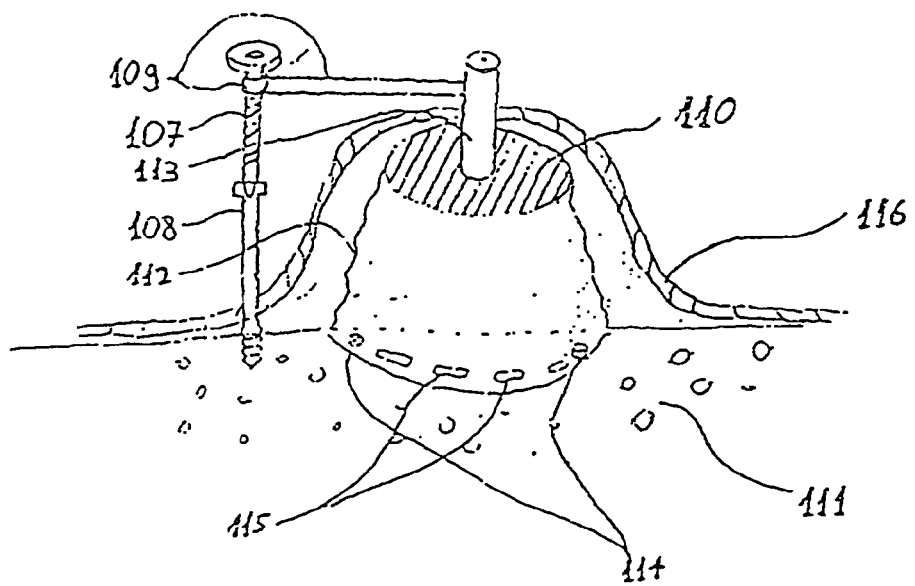
FIG. 8 is a perspective view illustrating the novel device used with accordance with the invention wherein the device of FIG. 5 is used with an external elevating screw.

In another preferred embodiment illustrated in FIG. 8 the elevating screw 107 can be placed outside the device as it is in external distractors. A base element 108 is fixated to the bone outside the region of the device. The plate 110 includes a lateral projection 109 outside the gums 116 and the elevating screw 107 passes through the projection 109 to the base element 108. When the screw 107 is activated, the plate 110 is displaced from the bone 111, the membrane 112 is unfolded and bone augmenting material can be inserted into the device through the tube 113. The membrane is fixated to the bone by screws or tacks 114 or by holes in the membrane 115 as described in FIG. 5A. The advantage of this device is that there is no screw in the region where bone is to be regenerated, therefore the rate of success is expected to be higher.

Figure 9:
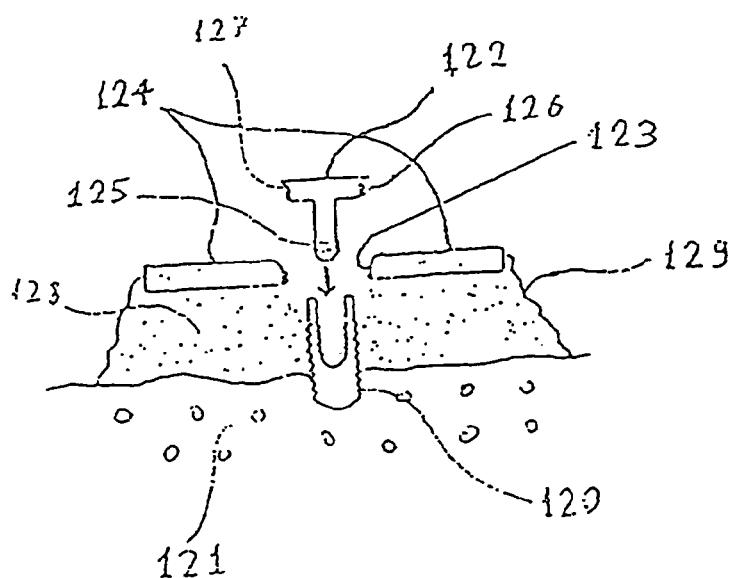
FIG. 9 is a sectional view illustrating the connection between the plate and a dental implant inserted at an early stage.

In another preferred embodiment the plate is configured to allow replacement of the elevating screw with the final bone implant without taking the device out. In this embodiment the bone implant can be inserted in an early phase and shorten the treatment time. The elevating screw is preferably narrow in order not to interfere with the process of bone regeneration and to reduce the hole in the gums. The final bone implant is preferably wide in order to have more surface attached to the bone. Therefore it is recommended to replace the elevating screw, which can be also perforated and hollow with a final bone implant or dental implant The replacement can be done after the device has reached its final dimension and the filling is complete. The tube in this embodiment is threaded to the plate and they are not one piece. The hole in the plate after removing the tube should be at least 3.8 mm to allow the insertion of a regular 3.75 mm dental implant. After the tube is removed from the plate the elevating screw is taken out through the hole in the plate and the final dental implant is inserted instead. FIG. 9 illustrates a sectional view of the device after the insertion of the final bone implant and before closing the hole in the plate. After the final dental implant 120 is inserted to the bone 121 a cover screw 122 is screwed inside the dental implant 120 (in the preferred case of an implant with an internal thread) and engaged the threads 123 in the hole of the plate 124. In this state, dental implant 120 stabilizes the plate 124. The cover screw 122 has one region 125 with threads that are compatible with the internal threads of the dental implant and a second region 126 that the threads fit the threads 123 of the hole in the plate and a region 127 that seals the connection between the plate and the cover screw. In this configuration for every dental implant in the market a special cover screw can be developed. After the insertion of the dental implant and the cover screw the bone is regenerated around the dental implant because the dental implant is surrounded by bone augmenting material 128 that is closed in the space created by the membrane 129. The process of osseointegration of the implant occurs simultaneously with the regeneration of the bone therefore the treatment is shorter.

In another preferred embodiment the plate described in the embodiments above is a rigid mesh and a bio-dissipative membrane is attached to the mesh and closes the holes of the mesh. The advantage of this configuration is that the plate with the mesh allows the filling of the device and prevents connective tissue to enter the space where bone is expected to regenerate, but after the membrane is resorbed blood vessels can enter from the periosteum and supply the new bone.

In all the embodiments where the titanium plate was mentioned connected to a membrane FIG. 5, 6, 7, 8, 9 the plate can be connected preferably to a perforated membrane that allows blood vessels to enter the cavity and give nutrition to the regenerating bone. In this embodiment the plate is preferably perforated like a titanium mesh with pore size of 0.2-1 mm. The device can be made only from the titanium plate without a membrane. As the titanium plate is distracted from the bone a cavity is created between the plate and the bone. This cavity can be filled with bone augmenting materials through the filling tubes. When the device has no membrane the holes in the plate can be even larger at the range of 0.5-2 mm. The filling can be done after each distraction or at the end when the plate reaches the final position.

The device can be sold to the dental surgeon connected to the membrane or without a membrane. In case the device is not connected to the membrane it allows the dental surgeon to choose the appropriate membrane. In this preferred embodiment the plate preferably includes holes or slots to allow the suturing of a membrane to the plate or to allow the connection of the membrane by clamps to the plate.

The devices described above being made from a plate and tubes are preferably sold to the dental surgeon separately and the dental surgeon is connecting them. This preferred embodiment is useful for insertion of the device in the tunnel technique. The surgeon first creates the subperiosteal tunnel then inserts the plate that can be connected to the membrane inside the tunnel. Perforates the gums above the device and connecting the tubes through the perforation to the device. The connection can be by screwing or bonding. The insertion of the plate without the tubes allows to insert the device to a lower tunnel which is more easy to perform and prevents tearing of the gums in the process of making the tunnel and in the insertion of the device.

In another preferred embodiment illustrated in FIG. 10 the use of regular dental implants 131 (FIG. 10C) and stabilizing elevating mechanism is implemented. Elevating abutments 138 (FIG. 10A) are threaded to the implants 131 through the tubes 132 of the plate 133 illustrated in FIG. 10B. The elevating abutments 138 have a slim extending rod 134 and a wider stop 135. The extending rods 134 have internal threads 136. Rings 140 with internal threads 141, external threads 142 and circular sealing edge 143 are threaded to the tubes 132. Hollow screws 145 (FIG. 10D) are threaded to the internal threads of the rings 141 till they touch the wider stop 135 of the elevating abutment 138. The hollow screws 145 have a wider diameter hollow space at their upper region 146. The extending rods 134 are inside the small diameter space 147 of the hollow screws 145. Nuts 150 (FIG. 10E) are threaded over the hollow screws till they touch the rings 140. Locking screws 155 (FIG. 10F) are threaded to the internal threads 136 of the extending rods 134 till they touch the stop 157 in the hollow screws.

In this embodiment the plate is stabilized to prevent micromotion. The locking screws 155 fixate the hollow screws 145 to the elevating abutments 138. The elevating abutments 138 are fixated to the dental implants 131 which are fixated to the bone. The nuts 150 are fixating the hollow screws 145 to the rings 140 which are fixated to the tubes 132 of the plate 133. When distraction of the plate 133 is needed the nuts 150 are unscrewed about 1 mm from the rings 140, the locking screws 155 are unscrewed to release the fixation of the hollow screws 145 and the hollow screws 145 are rotated. Since the hollow screws 145 are touching the wider stop 135 of the elevating abutments 138 the hollow screws 145 can't move towards the dental implants 131 so they are elevating the rings 140 which are threaded to the hollow screws 145. The rings 140 which are fixated to the tubes 132 of the plate 133 therefore elevate the plate 133. The plate 133 is elevated till the rings 140 touch the nuts 150. The plate 133 preferably is curved and not flat so it can fit the alveolar ridge, which is usually not flat. When the plate is intended to fit the alveolar ridge of the mouth the plate is curved in the bucco-lingual plane as can be seen in FIG. 11. FIG. 11 is a sectional view of the device placed in the jaws. The plate 133 is curved to fit the bone 160 of the alveolar ridge. The gums 161 are covering the plate and the tube 132 is protruding through the gums 161. The space between the plate 133 and the bone at the insertion of the device is preferably as small as possible to eliminate the need to stretch the gums. A curved plate allows good fining of the device to the bone. FIG. 12 is a perspective view of the device demonstrating the curved plate 133 and the tubes 132. The plate preferably has some small holes 163 on its edge to allow suturing of a membrane around the plate as it is illustrated for the plates of FIGS. 5, 6, 8, 9. The plate preferably has slots 165 at the connection between the tubes 132 and the plate 133 to increase the space between the plate and the dental implant to facilitate the insertion of bone substitute material. The slots 165 allow the insertion of bone substitute materials without significant elevation of the plate above the dental implant therefore the stretching of the gums is reduced and number of elevating sessions is reduced.

FIG. 13 illustrates the assembling of all the parts of FIG. 10 without the membrane. The device has two tubes 132 and it is placed on two dental implants 131. For illustrating the assembling the right side of the device is showing perspective view and the left side a sectional view. FIG. 13A illustrates the device after insertion before the process of gradual distraction of the gums 161. The plate is at the bone level 170, the rings 140 are screwed to the tubes 132, the hollow screws 145 are screwed to the rings 140 over the extending rods 134. The plate is below the gums 161 and above the bone level touching the bone. The tubes 132 are protruding through the gums to the oral cavity. The fact that the tubes are part of the plate and are moving with the plate allows to use short tubes that can fit to all cases. The nuts 150 are screwed over the hollow screws 145 till they touch the rings 150 to prevent micro-motion between the plate and the hollow screws. The locking screws 155 are fixating the hollow screw 145 to the extending rods 134 therefore the device is fixated to the dental implants 131 and to the bone and micro-motion is prevented between the plate and the bone. FIG. 13B is illustrating the device at the end of the elevating process. A space is created between the plate 133 and the bone that can be filled with bone augmenting material. The filling can be after each elevation or at the end. After filling the space preferably the elevation mechanism can be replaced with a stabilizing mechanism. The parts of the elevating mechanism to be replaced are the elevating rods 138, the hollows screws 145, the nuts 150 and the locking screws 155. The stabilizing mechanism is illustrated in FIG. 13C. The stabilizing mechanism includes a stabilizing abutments 172 that are screwed to the dental implants 131. The stabilizing abutments 172 have internal threads in their upper region to fit the fixating screws 173. The fixating screws 173 are fixating the rings 140 to the stabilizing abutments 172 and therefore stabilize the plate 133 and prevents micro-motion. The stabilizing mechanism is also a sealing mechanism to prevent the entrance of infection through the tubes to the space below the plate.

In another preferred embodiment there is no need for the elevating abutment. The hollow screw is seated over the dental implant and fixated to the implant by a fixating screw in the same way abutments are fixated to dental implants. (The hollow screw has internal narrower region close to the region which is adjacent the implant and the head of the fixating screw is wider than this narrow region, so when the fixating screw is screwed through the hollow screw inside the dental implant the hollow screw is fixated to the implant.) The hollow screw has no anti rotational element in its contact region with the implant to allow the rotation of the screw and therefore the distraction of the plate from the bone. In order to allow the rotation of the hollow screw the fixating screw and the stabilizing nut have to be released.

It is important that the plate wilt not have sharp edges and to have slopes 175 between the tubes and the plate borders. Rounded borders and slopes will prevent perforations of the gums and exposure of the plate to the oral cavity. The plate can be in the shape of a circular cone or oval cone in the preferred embodiment of one plate over one dental implant. The surface of the plate can be different at different region of the plate. The region of the plate facing the bone preferably is rough to allow good adhesion of the blood clot for example S.L.A surface of Straumann, Osseotite surface of 3I, Tiunite of Branernark or HA surface. The region of the plate facing the gums is preferably also rough like the plate or rough to a limited degree to allow good adhesion of the periosteal tissue to the p late in order to prevent slipping of the tissue while distracting the device. The surface of the plate near the tubes and the tubes in one preferred embodiment are smooth or acid etched to prevent plaque accumulation. In another preferred embodiment the surface of the plate near the tubes and the tubes are rough to enhance the adhesion of the gums to the tubes. Preferably the tube is not straight but also has external protrusions or at least one circular wider ring to improve the adhesion of the gums and prevent the slipping of the gums when the device is distracted.

Another important feature of the device is its increase in vertical dimension along the distraction process. If the device is enlarged along the distraction process the device can reach the teeth of the opposing jaw and the process of distraction is stopped. If A is the distance between the most upper point of the device and the bone before the distraction process and B is the distance between the most upper point of the device and the bone after the distraction process and C is the distraction of the device meaning the path of the plate then B is preferably less than A+C. Preferably A=B as it is in the device of FIG. 13. The height of the device of FIG. 13B is the same as the height of the device of FIG. 13A and it is the height of the device along the distraction process. The height of the device of FIG. 13C after the replacement of the elevating mechanism is even smaller.

In another preferred embodiment the elevating mechanism can be based on adding components above the dental implants instead of screwing. For example it is possible to screw to the dental implant a primary abutment that its lower region having a screw to fit the internal threads of the dental implant and its upper region having internal threads. To this primary abutment it is possible now to connect secondary abutments. The secondary abutment has on its lower region a screw to fit the internal threads of the abutment and on its upper region internal threads as it is for the primary abutment. In this design it is possible to screw the secondary abutment to the primary abutment or to a secondary abutment. Each time a secondary abutment is screwed to the previous abutment and a sealing screw is screwed to the most upper abutment through the rings 40 of the device of FIG. 13 the plate is elevated. Preferably each abutment is elevating the plate by 1 mm. The head of the sealing screw is wider than the rings so the device is sealed to prevent the entrance of infection from the oral cavity. In the device of FIG. 10-13 it is possible to place an elastic impression material over the protruding elements to seal the device.

The insertion of the device can be by raising a flap, insertion of the dental implants, placement of the device and suturing the gums above the device. Another way to prevent suturing above the device is by incising at the vestibulum, raising a flap and perforating the flap to insert the tubes of the device and the flap is suture above bone and not above the device. Preferably the device is inserted by using the tunnel technique. A subperiosteal tunnel is created along the alveolar ridge, the gums are perforated at the crest at the desired location, the plate is inserted, the implants are inserted through the tubes and the elevating mechanism is installed. In order to perforate the gums it is possible to insert small tubes with conical caps to the tunnel connected to a wire and to pull them through the gums. It is recommended to perforate the cortical bone. This can be done though the tubes of the plate or preferably through the small tubes inserted to perforate the gums. While using the tunnel technique it is possible to attach a membrane to the device as it is for the device described above. If a membrane is connected to the device preferably the membrane is perforated at its edges to allow fixation of the membrane as described in FIG. 5A. In another preferred embodiment using the tunnel technique the tubes can be connected to the plate after the insertion of the plate. Preferably the plate has threads and the tubes are threaded to the plate through the gums. The fact that the plate is inserted without the tubes allows to insert the plate without significant stretching of the gums therefore insertion is simpler and damage to the gums is prevented. It is important to verify that the connection between the tubes and the plate is sealed and infection can't penetrate through this connection.

The filling conduit of the devices described above for example the tubes of the plate preferably have internal threads for a sealing screw and for the connection to a filling syringe. The filling conduit preferably has another sealing component preferably a valve that is open while filling the pouch or the space of the device and is closed otherwise. The chamber between the two sealing components the screw and the valve is preferably filled with biocompatible antiseptic material like chlorhexedine gel or calcium-hydroxide. The antiseptic material should be washed out before filling and put again when the cannula is closed. The syringe to be connected to the filling conduit is preferably filled with bone augmenting material in gelatinous consistency or suspension. The filling material can be an autograft, an allograft, a xenograft, an alloplast, a cytokine, a hormone, a growth factor, a physiologically acceptable drug, a biological modifier, a protein, an antigen, a cell chemotaxis stimulator material, a material inducing osteogenes is, an osteoinduction material, an osteoconduction material, a bioactive material, a bioresorbable material, a bioabsorbable material, a biodegradable material and any combination thereof The filling material preferably includes materials that occupy a space in the body for at least several months. These materials preferably encourage the tissue to grow inside the space occupied by the filling material. This is the principle function of most bone augmenting materials available on the market. Preferably the bone augmenting material is resorbable. The filling material can be augmenting bone material available in the market like hydroxyapatite, bovine mineral (i.e. Bio-Oss available from Geistlich, Swiss), demineralized frized dried bone allograft, synthetic materials like PLA (i.e. FisioGraft from Ghimas) or suspension of bovine mineral in a liquid medium like PepGen 15 Flow from Ceramed. The filling material can be also fully or partially not bioresorbable if the procedure is done only for aesthetic reason and implants are not going to be inserted, for example crystal hydroxyapetit.

The filling material can include therapeutic materials and can include self-expanding materials from the list mentioned above. Many of the bone augmenting materials have the tendency to expand when getting wet by hydration.

The foregoing procedure has been described in terms of the mandible. Of course, the same procedure can also be applied to reconstruction of the maxilla and other bones and for other tissues in the body.

In another preferred embodiment a similar device can be inserted into the lips or breast filled with material that stimutate fat tissue regeneration or connective tissue regeneration resulting in enlargement of these organs. In these embodiments the pouch is preferably perforated and it is filled with fat cells. The fat cells can be sucked from another region in the body were there is excess of fat or can be stem cells. The perforations are to allow rapid vascularization of the cells. The advantage of using fat cells over silicon gels is that there are no side effects of silicon. Fat injection is a known treatment that has two basic drawbacks. One is that it is difficult to control the shape of the fat after injections resulting in not smooth appearance. The second problem is that fat injection has a tendency to have calcified regions in them that resembles calcifications in breast cancer. The treatment with fat injections demands many injections all around the breast in order to control the shape of the breast. Women that have received this kind of treatment needs many biopsies because the calcifications all around the breast look like cancer in mammography. In the present invention the fat is placed in one known place and the shape can be controlled. Several successive introductions of fat cells will act as a tissue expander. The use of resorbable perforated tissue expander will eliminate the need for a second surgery for taking out the tissue expander. The pouch can be filled with slowly bioresorbable collagen. The perforations in the pouch are at the range of several hundreds of microns preferably of 0.5 mm to allow tissue to enter inside the pouch.

Another preferred embodiment is to use a device that the filling element for example the cannula is made of two parts one is external made of nonresorbable material and the second is internal made of bioresorbable material. The border between the two is preferably the slot. In this device it is easy to take the nonresorbable part out by twisting the cannula and leaving the bioresorbable inside the body.

Another preferred embodiment of the device and method is bone augmentation of the maxillary sinus called also sinus lift. This procedure is done when the alveolar ridge beneath the maxillary sinus is too short—less then 8 mm height. The floor of the sinus is lined with a delicate membrane called the Schneiderian membrane. Beneath the floor of the sinus there is the short alveolar ridge covered by the gums.

The inflatable device like the device of FIG. 3 can be inserted through the alveolar ridge to the sinus below the Schneiderian membrane or through the buccal wall of the maxillary sinus to be lateral and below the Schneiderian membrane. The perforated side of the device is facing the bone of the floor of the sinus and the non-perforated region or the less perforated region is facing the Schneiderian membrane and preferably the opening in the wall of the sinus. When the pouch is filled with bone augmenting material the Schneiderian membrane is raised and the bone augmenting material is in contact with the bone.

In another preferred embodiment the filling conduit is made from a bio-dissipative cloth like material which is pushed inside the sinus after the filling of the pouch.

The pouch of the device is preferably made of collagen or other Bioresorbable material and the cannula is preferably a hollow dental implant. The device has preferably two sealing components a screw and a valve. The pouch can be fully or partially packed inside the hollow implant.

In another preferred embodiment the upper region of the pouch is connected to resorbable cord. The cord is protruding through the osteotomy and can be slowly allowed to get inside the sinus. This method allows to control the vertical enlargement of the pouch. If the pouch is not allowed to grow vertically it will grow horizontally therefore the raising of the Schneiderian membrane will be more efficient and safe.

In another preferred embodiment the lower region of the pouch can be easily detached from the upper region. The two regions can be connected by a suture that can be pulled out. The lower region can be connected to the filling conduit so when the filling conduit is taken out the lower region is coming out also leaving the bone augmenting material with direct contact with the floor of the sinus. In this embodiment the lower region can be not resorbable.

In another embodiment the filling conduit is a hollow bone implant that can be left in place and serve in the future to support a dental prosthesis.

Figure 17:
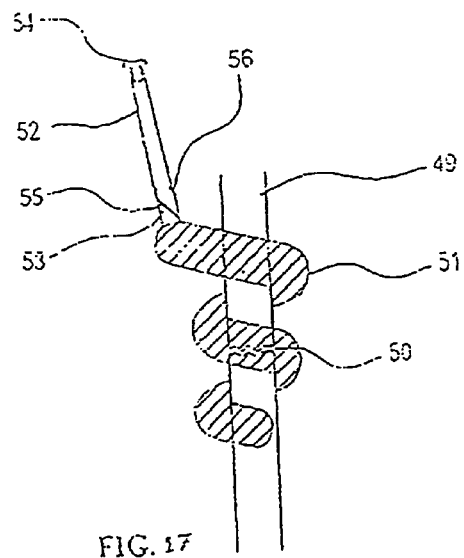
FIG. 17 is a perspective view illustrating the device for external fixation of long bones.

In another preferred device illustrated in FIG. 17 the pouch is in the shape of a coil 51. This configuration is particularly useful for the fixation of tissues especially of a fracture 50 in a bone 49. This pouch is to be placed around the fracture and it is connected to a catheter 53 (filling conduit) made of bioresorbable material that has a bioresorbable valve 55. The external part of the catheter 52 is made of nonresorbable material and has a sealing component a screw 54. There is a slot 56 in the catheter, which is the braking point for taking the catheter out after finishing all the filling of the pouch. The device can be made from different kinds of bioabsorbable materials as described before.

The filling of the pouch is with a biocompatible material that sets and becomes rigid inside the tissue. After the material has set the bone fragments near the fracture are fixated. Preferably the biocompatible filling material is a bioresorbable material that contains materials assisting in the process of bone healing like bone cements available on the market today, for example Skeletal Repair System (SRS) from Norian company, Healos from Orquest company, OsteoGenics and Orthovita's Orthocomp from Howmedical Leibinger company.

This procedure assists in shaping the bone cement and prevents its migration from the site of application. The coiled pouch has preferably perforated region in the internal aspect of the pouch facing the bone and less perforated or non perforated region facing the surrounding tissues. The perforated inner region is designed to allow some minor leakage of the cement under pressure to come in contact and adhere to the bone so after the cement is set the bone fragments are fixated. There is one mass of rigid cement connecting the bone fragments through the internal space of the device. This unique feature is distinguishing the present inflatable device from all prior art inflatable devices which prevent the formation of a continues mass from the internal aspect of the device to the surrounding tissues and the mechanical connection between two tissues like bone fragments. The external region can be also perforated but preferably the external region is less perforated to prevent leakage of the cement under pressure but to allow nutrition, blood supply and tissue ingrowth. If the cement is not Bioresorbable the external region is preferably not perforated.

Figure 14:
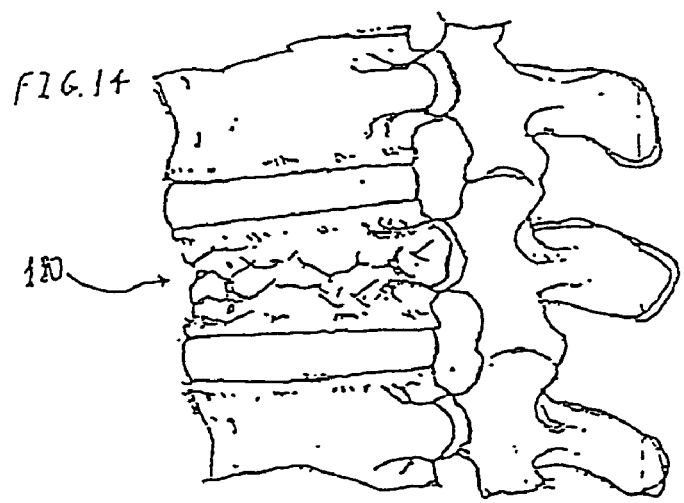
FIG. 14 is a side view illustrating a crushed vertebra.
Figure 15:
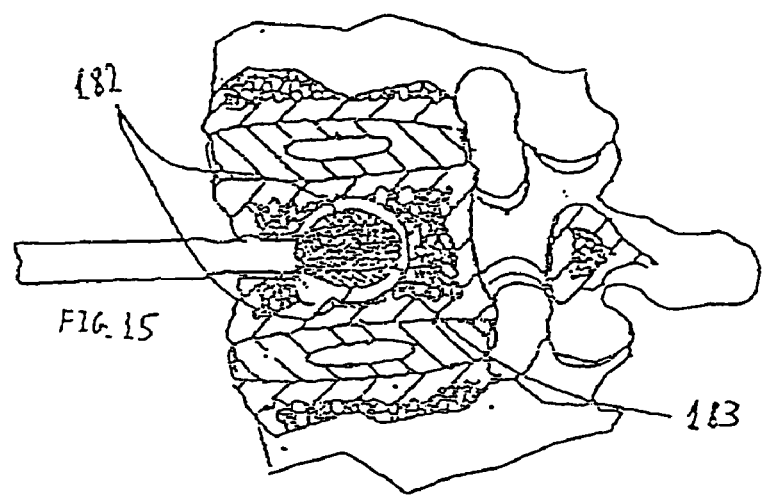
FIG. 15 is sectional view illustrated the novel device inside the crushed vertebra.
Figure 16:
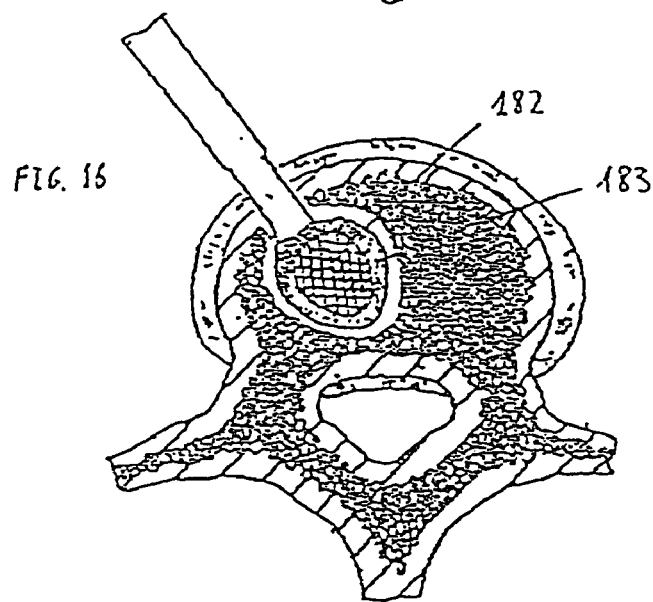
FIG. 16 is a sectional view illustrating the device inside the vertebra from above.

In another preferred embodiment the inflatable element can be used in cementoplastia. The device is inserted into a bone cavity like a bone cyst or a bone that suffers from osteoporosis. A bone cyst is a pathologic phenomena that a cavity is created inside the bone. Sometimes the cyst contains liquid and is surrounded by a membrane. The cyst has a tendency to grow resulting in thinning of the walls of the bone around the cyst that leads to pathologic fractures. Filling the inflatable element with a bone augmenting material can lead to healing of the cyst. Bone augmenting materials are materials that occupy a space in the body for several months and encourage the bone to grow inside this space and replace the bone augmenting material. In a preferred embodiment the filling bone augmenting material is a bone cement tat sets inside the inflatable element. Filling of the cyst with a hard material strengthens the bone and reduces the risk of pathologic fracture, which is the main complication in bone cysts and osteoporosis. It is also possible to fill the cyst with the bone cement without the use of the inflatable element but then the cement can leak outside the bone and can penetrate into blood vessels and nerves. In another preferred embodiment the inflatable element can be configured to allow direct contact between the surrounding tissue and the filling material. In a preferred embodiment the inflatable element is perforated with small holes that allow for a little amount of the bone cement to traverse the wall of the inflatable element and touch the bone. In this embodiment the chance of major leaking and entrance into blood vessels is reduced and the filling material is immediately touching the bone and starts its activity. In another preferred embodiment the inflatable element is made from at least two areas one which is perforated, to be faced against the bone and a second area, which is not perforated, to be faced against other tissues like blood vessels and nerves. This embodiment is particularly useful for vertebroplasty and kyphoplasty. In these procedures a bone cement is inserted into a crushed vertebra. The cement is connecting the lower segment and the upper segment of the crushed vertebra so they cannot move against each other. When the bone segments stop moving the pain is significantly relieved and healing is faster. The problem with these procedures is that the cement can leak inside the spinal cord and blood vessels. By using an inflatable element which has one region, which is not perforated, that faces the spinal cord and another region, which is, perforated that faces the bone segments the vertebroplasty can be done safely. In kyphoplasty the bone segments are displaced to their original position before the crushing of the vertebra, by balloons and afterwards the bone cement is inserted. In the preferred embodiment described above kyphoplasty can be done also with no need for another balloon to displace the bone fragments. The inflatable element as being filled with the bone cement is displacing the bone fragments. This makes the procedure shorter simpler and safer. FIG. 14 illustrates a crushed vertebra 180. FIG. 15 illustrates a longitudinal section of the vertebra revealing the inflatable device after its insertion inside the crushed vertebra. The vertebra can be reamed before the insertion to facilitate the insertion. The inflatable pouch has perforated regions 182 facing the upper and lower regions and a sealed region 183 facing the horizontal plane protecting the spinal cord and the surrounding blood vessel. FIG. 16 illustrates the device in an horizontal section through the vertebra The inflatable element can be made from non-resorbable materials since it has a perforated area. In a preferred embodiment the inflatable element is made at least in part from bio-dissipative material. The principal function is to allow contact between the filling material and the surrounding tissue. Contact can be achieved by using a perforated inflatable element or by using a bio-dissipative material as part of the inflatable element. These procedures can be done between any two bone fragments. The inflatable element is place between the bone fragments and/or around them so the perforated region is facing the bone fragments and the non-perforated region is facing the surrounding tissues. The device can be inserted inside bone cavities created by malignant metastases. In these cases the cortex of the cavity is many times destroyed so cementoplastia is contraindicated because of the risk of cement leakage. Using the perforated inflatable device with bone cement can prevent the leakage, strengthen the bone and reduce the pain associated with this pathology. The pore size of the inflatable element should be fitted to the cement consistency. In a preferred embodiment the pore size is designed to control the leakage by controlling the pressure. In a preferred embodiment the inflatable element can have several sizes of pores and by using a cement in a known consistency it is possible to control by the pressure of the cement when the cement is leaking through the large pores and when from the smaller pores. In another preferred embodiment monitoring the pressure can show when leaking is started. When leaking is started although cement is inserted the pressure is not rising proportionally. When the surgeon is getting this signal he can stop injecting the cement therefore the risk for damaging leakage is significantly reduced. This monitoring and stopping the injection can be done automaticly using an automatic injecting machine that is monitoring the pressure inside the syringe and programmed to stop when the pressure is not rising proportionally to the injection. For kyphoplasty the device should have pore size and cement consistency to allow pressure in the range of 200-360 PSI. In this pressure the bone fragment can be displaced. As the bone fragments are displaced there will be a decrease in the pressure. The surgeon by monitoring the vertebra by X-Ray can identify if the decreased pressure is because the vertebra is opened and to continue the injection or the decreased pressure is because of leakage and to stop the injection of the cement.

In another embodiment the inflatable device can be placed between two vertebras in cases of damage to the disc. Inflation of the device can displace the vertebras and the cement leaking through the perforated regions will fixate the vertebras in their new position. For this spinal fusion preferably the upper and lower region are perforated to allow leakage of the cement under pressure and the region facing the horizontal plane prevent leakage towards the spine and the blood vessels.

The inflatable element is preferably configured to stabilize the bone fragments. In one embodiment the shape of the inflatable is a coil like in FIG. 17 but it can be also like a double walled sleeve placed so the bone fragments are inside the sleeve or in the shape of a double walled sheet that can be placed around the bone fragments. The bone fragments are attached to the cement that is leaking through the little holes and the shape of the cement after setting is fixating the bone fragments and strengthen the fracture region. The size of the holes in the inflatable element should be compatible with the filling material. The holes should allow a minor leakage and direct contact between the leaking material to the material inside the device. The leakage must be possible only for less then 2 mm from the device when there is pressure that is sufficient to displace the bone fragments. Preferably only wetting of the external surface of the pouch is allowed. The contact between the material inside and outside the device improves the stabilization and prevents migration of the filling material.

Figure 18:
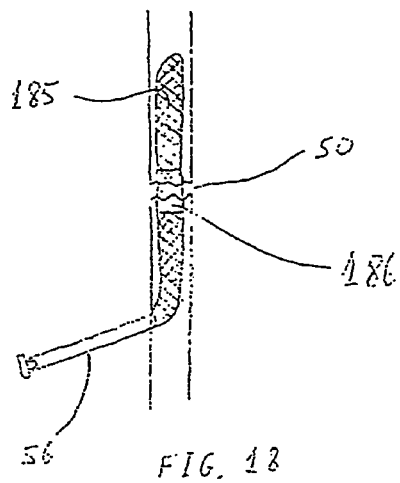
FIG. 18 is a sectional view illustrating the device for internal fixation of long bones.

In another embodiment the device can be used for treatment of fractures of long bones internally. FIG. 18 illustrates a fracture like the fracture of FIG. 17. The inflatable perforated pouch 185 is inserted inside the bone after preparing a cavity in the bone below the fracture 50 and across the fracture to reach the bone above the fracture. After the cement is injected through the filling conduit 56 and some minor leakage of the cement through the holes the bone fragments are fixated. If there is significant damage to the cortical bone the pouch can include a sealed region 186 to prevent leakage of the cement. The filling of the pouch under pressure can align the bone fragments.

Figure 19:
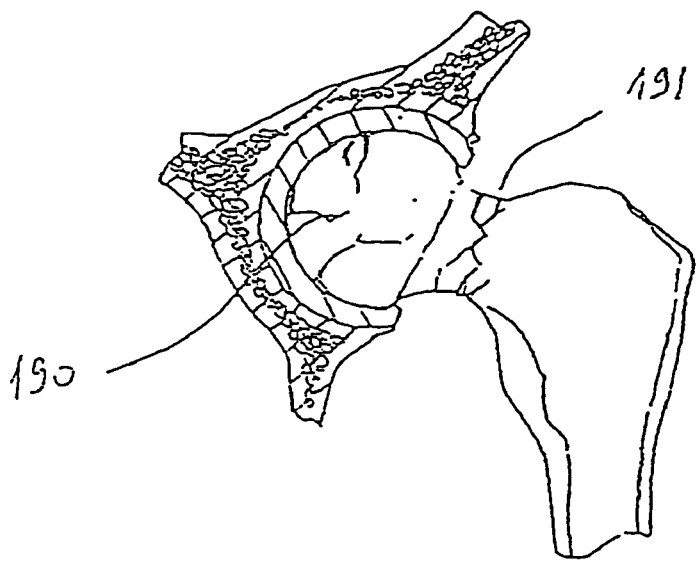
FIG. 19 is side view of the femur joint with a fracture.
Figure 20:
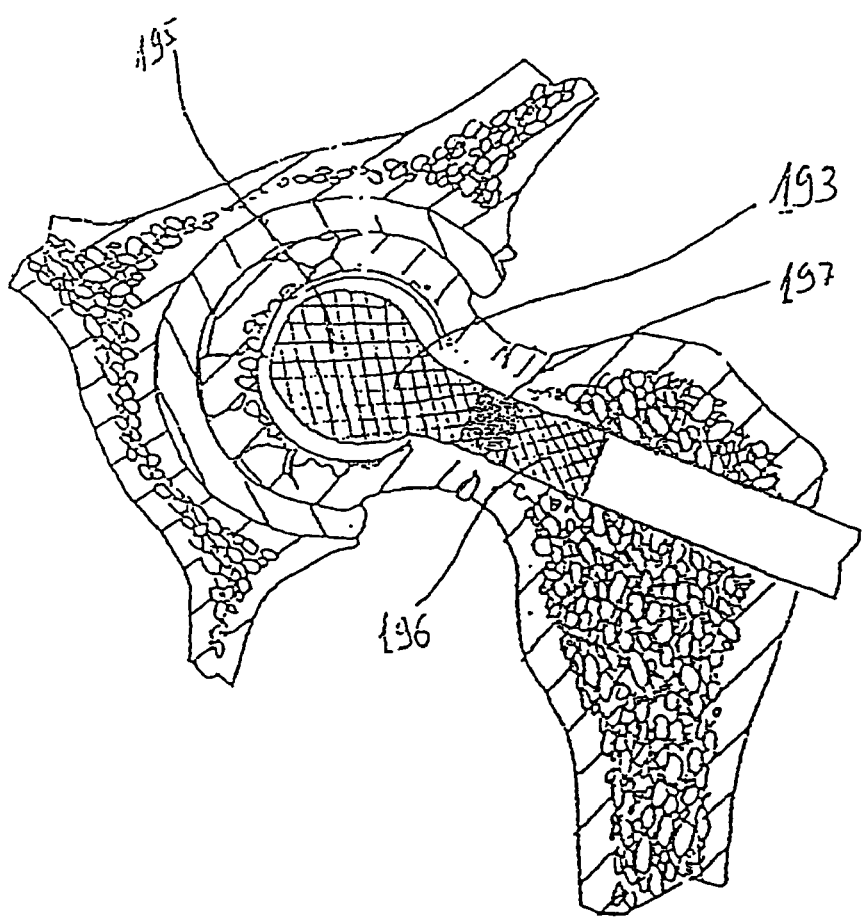
FIG. 20 is a sectional view illustrating the novel device inside the hip of FIG. 19.

In another preferred embodiment the perforated inflatable pouch can be used to treat avascular necrosis of the femoral head or fractures of the neck of the femur or for prevention of fractures. FIG. 19 illustrates a hip with avascular necrosis of the femoral head 190 and fracture of the neck of the femur 191. FIG. 20 illustrates the pouch 193 inside the bone after preparing the cavity. The pouch has rounded region 195 to fit the femoral head and an elongated region 196 to fit the neck. If the fracture is involved with significant damage to the cortical plate the pouch preferably includes a less perforated region 197 to be placed against the fracture to prevent leakage. The preferred design of the device is an elongated pouch which is perforated to allow contact between the cement and the surrounding bone. The size of pores are of the size 0.3-2 mm. The pouch has a non perforated ring approximately at the middle of the pouch surrounding the pouch and splitting the device into two parts one perforated pouch distal to the ring and one perforated pouch proximal to the ring. The ring can be part of the device or can be connected over the pouch. The ring can be non perforated or preferably perforated with small holes. The small holes allow tissue ingrowth but prevent leakage of the cement. The size of the pores are preferably 30-250 micron. Preferably in all the embodiments to allow precise placement of the less perforated region it should be distinguished in X-Ray from the perforated region. This can be achieved by adding a radiopaque material like barium to the non perforated region.

The device can be used for preventing fractures in patients with advanced osteoporosis. In these cases the device is inserted inside the hip before the fracture occures and strengthen the bone by the cement.

Figure 21:
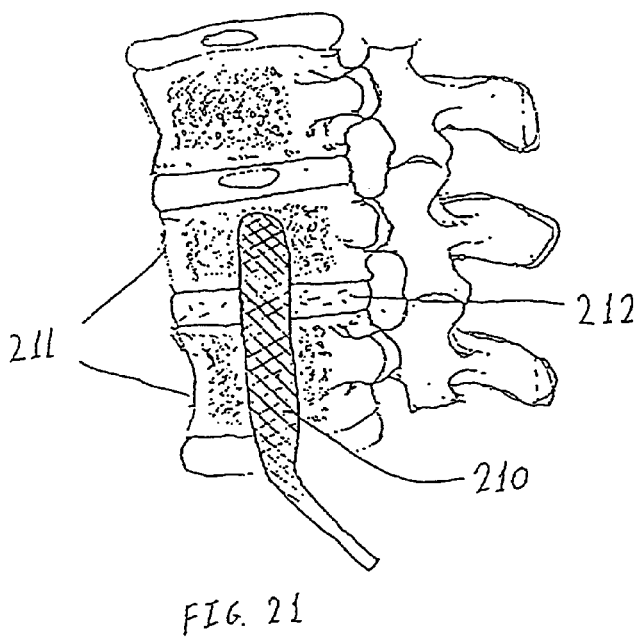
FIG. 21 is a sectional view illustrating the device going through a disc between adjacent vertebras.

In another preferred embodiment the novel device can be used for spinal fusion. FIG. 21 illustrates a longitudinal inflatable pouch 210 inserted through two adjacent vertebras 211 and the deteriorated disc 212 between them. The cavity for the device is created first coming from below. The entrance to the body can be from anterior or from posterior. After the cavity is prepared the device is inserted and filled with the cement. As the cement sets the vertebras are fixated leading to spinal fusion. In a preferred embodiment the pouch is perforated to allow some degree of cement leakage to achieve improved stabilization. Preferably the pouch has a non perforated region in the middle at the region between the vertebras to prevent leakage of the cement. The pouch and the cement can be Bioresorbable leading to bone tissue ingrowth inside the space of the inflatable pouch.

The perforated pouch allowing the cement to leak can be used in other fractures like tibial plateau fracture, distal radius, long bone fractures, elbow etc'.

Figures 22A, 22B:
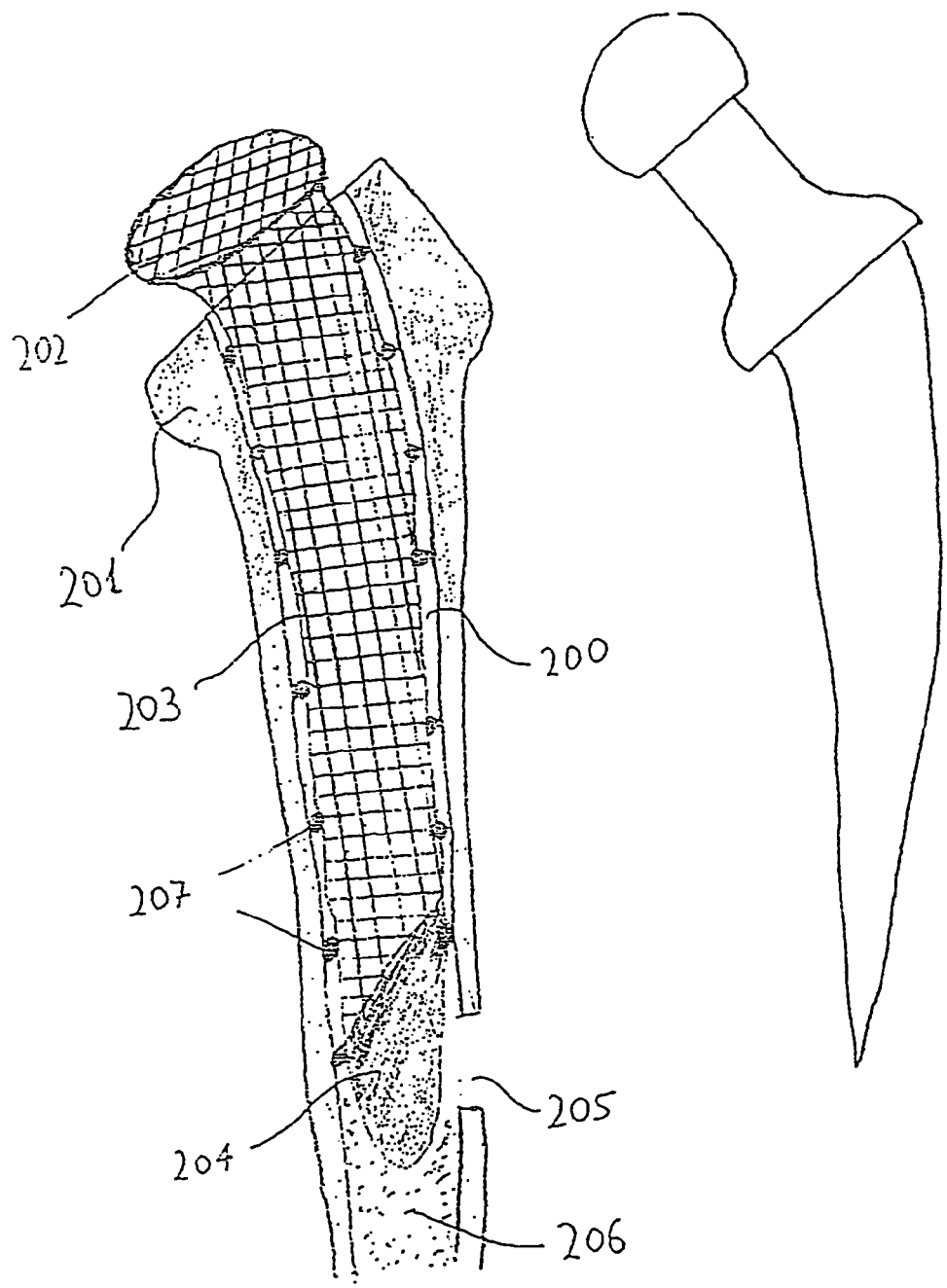
FIG. 22A is a sectional view illustrating the novel device for cementing artificial joints.
FIG. 22B is a sectional view of the hip stem of the artificial joint.

In another preferred embodiment the device can be used in joint replacement procedures. In some of these procedures a longitudinal cavity is created inside the bone before the artificial, joint is cemented inside the bone. In some cases a distal opening is created in the distal region of the bone to facilitate the creation of the cavity. In order to achieve good stabilization the cement has to be pressurized inside the bone before insertion of the stem of the prosthetic joint. In many cases this procedure is associated with leakage of cement or fat that can cause pulmonary embolism. The cement can also migrate along the bone or through the distal opening. In order to overcome this problem cement restrictors or plugs are inserted inside the bone. In the novel method illustrated in FIG. 22A after the cavity 200 in the bone 201 is created the inflatable element 202 is inserted inside the cavity. The inflatable element 202 is preferably in the shape of an elongated narrow pouch. The walls 203 of this pouch are perforated to allow minor leakage of cement under pressure to allow the entrance of cement inside the walls of the bone. This pouch preferably has one region 204 that is not perforated to prevent leakage of the cement. The non perforated region 204 is preferably located in the distal region of the pouch facing the distal opening 205 and the distal region of the cavity 206. After the insertion of the pouch the pouch is filled with cement under pressure and the prosthetic joint illustrated in FIG. 22B is inserted inside the pouch, which is inside the bone cavity. The excess of cement will move proximally so the surgeon can see and take it away. The pouch prevents the leakage in other directions except for minor leakage to touch and penetrate the bone walls. The non perforated region 204 function as the cement restrictor. The use of a soft pliable material as the cement restrictor eliminates the need to have many sizes of restrictors and the need to fit them precisely inside the bone.

Another property of the device is to control the width of the cement layer. The ideal width is about 1 mm. If the cement mantle is too narrow cracks can be developed leading to loosening of the artificial joint. The novel pouch preferably has several small regions 207 along the surface of the pouch that are about 1 mm width. These regions prevent the stem from touching the bone and take care that the width of the cement mantle is about 1 mm. The dimension of these regions parallel to the plane of the pouch are preferably less that 1 mm in order not to reduce the contact of the cement and the bone. The pouch can be fully or partially Bioresorbable as it is the case in all the embodiments described above. The pouch is preferably made from materials that can strengthen the cement or materials that can be chemically connected to the cement. In another preferred embodiment the pores in the pouch can be with different sizes. The pores in the distal region are larger and became gradually smaller towards the mesial region from which the artificial joint is inserted. Gradual change of the pore size can control the path of the cement leakage from the pouch. At the beginning the cement will leak at the distal region 206 and as the pressure is rising the cement will leak more proximally. This process will eliminate air capture in the cement mantle.

In another embodiment the device can be used to allow selective release of drugs. The inflatable pouch can be inserted between two tissues so the perforated region is facing one tissue and the non perforated region is facing the other tissue. When the medication is injected inside the pouch the medication is leaking through the perforated region and influence one tissue and not the other tissue. This embodiment is of particular use for the use of toxic medications for malignant tissues. The device allows the direct contact between the malignant tissue and the drug while preventing contact with the surrounding healthy tissues. The device can be in the shape of a double walled sleeve, the internal wall of the sleeve is perforated and the external wall is not. The device is placed to surround the tissue to be treated. When the medications are inserted they leak through the internal wall towards the treated tissue and the other tissues are protected from the influence of the toxic drug. In these embodiment the pore size can be smaller then size of the pores in the embodiments above. The pore sizes are to be compatible with the drug.

In all the embodiments that describe an inflatable container having at least one penetrable or perforated region and one less penetrable or sealed region there can be several embodiments as regard to the stiffness of each region. In one preferred embodiment the less penetrable region is stiffer than the penetrable region in order to allow control over the shape of the device when inflated. In another preferred embodiment both regions have substantially the same stiffness and therefore the surrounding tissue is dictating the shape the device will have after inflating. In another preferred embodiment the less penetrable or sealed region is less stiff than the penetrable region so the less penetrable region is in close contact with the bone and assuring the discontinuity of the bone is more protected from leakage. In the preferred embodiment of the device inside the vertebra the sealed circumferential region is less stiff than the rest of the device so the fracture zone is more protected.

Although the present invention has been described and illustrated in the context of certain preferred embodiments, it will be understood that modifications may be made without departing from the spirit of the invention.

What is claimed is:

1. A guided bone regeneration system for augmenting bone between the bone and the periosteal tissue comprising:
    a device in the shape of an expandable pouch before being inserted inside the body for insertion between the bone and its periosteal tissues, and;
    a bone augmenting material, at least part of said bone augmenting material is bio-dissipative, all the bottom of said pouch, before being inserted inside said body is resistant to the passage of said bone augmenting material from inside said pouch downwards to beneath said pouch, said pouch before being inserted inside said body has at said bottom towards said bone a first substantially horizontal bone-contacting region which is perforated with more than one hole that allow bone tissue ingrowth and a second substantially horizontal periosteal tissue-contacting region at the top of said pouch towards said periosteal tissue which is resistant to epithelial tissue ingrowth, holes that allow epithelial tissue ingrowth are absent in said second region, wherein said pouch is filled with said bone augmenting material, said first region being configured, before being inserted inside the body, to retain said bone augmenting material within said pouch, wherein said holes are sized according to said bone augmenting material to resist the passage of said bone augmenting material through said holes, wherein said pouch is configured so said first region exhibits a first mean time to dispersion and said second region exhibits a second mean time to dispersion longer than said first mean time to dispersion, and wherein said pouch is being designed to allow bone tissue ingrowth through only one side of said pouch and to block epithelial tissue ingrowth through other sides of said pouch.

2. The system of claim 1, wherein said pouch includes at least one fill opening into which said bone augmenting material may be inserted.

3. The system of claim 1, wherein said first region of said pouch is made at least partially from a bio-dissipative material.

4. The system of claim 1, wherein said bone augmenting material includes rigid particles.

5. The system of claim 1, wherein said pouch includes a filling conduit.

6. The system of claim 1, wherein said second region is made from a guided bone regeneration membrane.

7. The system of claim 1, wherein said pouch includes a rigid region and a flexible region.

8. The system of claim 7, wherein said rigid region is part of said second region.

9. The system of claim 1, wherein said pouch includes an extension for fixation, said extension has at least one hole.

10. The system of claim 1, wherein the most lower area of said pouch, before being inserted inside the body, is resistant to passage of at least part of said bone augmenting material.

11. The system of claim 1, wherein an aperture which is large enough to allow the passage of all said bone augmenting material through said aperture is absent from said bottom of said pouch.

* * * * *